US005703081A

United States Patent [19]
Miyake et al.

[11] Patent Number: 5,703,081
[45] Date of Patent: Dec. 30, 1997

[54] QUINOLONECARBOXYLIC ACID DERIVATIVES, THEIR PRODUCTION AND USE

[75] Inventors: Akio Miyake, Hirakata; Masahira Nakamura, Kashiba-cho; Hideto Fukushi, Osaka, all of Japan

[73] Assignee: Takeda Chemical Industries, Ltd., Osaka, Japan

[21] Appl. No.: 608,697

[22] Filed: Feb. 29, 1996

Related U.S. Application Data

[62] Division of Ser. No. 207,091, Mar. 8, 1994, Pat. No. 5,519,024.

[30] Foreign Application Priority Data

Mar. 9, 1993 [JP] Japan ................................. 5-047917

[51] Int. Cl.$^6$ .................. A61K 31/495; A61K 31/47; C07D 401/02; C07D 215/56
[52] U.S. Cl. .................. 514/254; 514/312; 544/363; 546/156
[58] Field of Search .................. 544/363; 546/156; 514/254, 312

[56] References Cited

U.S. PATENT DOCUMENTS

| | | | |
|---|---|---|---|
| 4,017,622 | 4/1977 | Minami et al. | 544/363 |
| 4,292,317 | 9/1981 | Pesson | 544/363 |
| 4,448,962 | 5/1984 | Arihura et al. | 544/362 |
| 5,420,140 | 5/1995 | Perrin | 514/312 |

FOREIGN PATENT DOCUMENTS

| | | |
|---|---|---|
| 92/16521 | 10/1992 | WIPO . |
| 92/18497 | 10/1992 | WIPO . |

OTHER PUBLICATIONS

Derwent CPI 92-382017/46 of WO 92/18497, 1992.

Derwent CPI 92-349129/42 of WO 92/16521, 1992.

Chemical Abstracts, vol. 108: 131600s, "Preparation of Quinolonecarboxylic Acid Derivatives as Medical Bactericides", N. Hirokazu et al., 1988.

Chemical Abstracts, vol. 106: 84642d, "Preparation of Antibacterial Piperazinylquinolinecarboxylic Acid Derivatives", I. Yasuo et al., 1987.

Chemical Abstracts, vol. 84: 59561w, "Piperazine Derivatives", M. Shinsaku et al., 1976.

Chemical Abstracts, vol. 116: 83514h, "Some Reactions of N-propdienyl-4-quinolones", R. Stanislav et al., 1992.

Chemical Abstracts, vol. 113: 231407f, "Preparation of Piperazinylquinolones and Analogs", K. Masatsune et al., 1990.

Ito et. al., Chem.Abstracts 106-84642; abstract of Jpn. Kokai 61218584 A2, Sep. 29, 1986, (1987).

Chemical Abstracts, 114-206981; abstract of Zhu et. al., Yaoxue Xuebao, 25(9), pp. 670-676 (1990), (1991).

*Primary Examiner*—Bernard Dentz
*Attorney, Agent, or Firm*—Wenderoth, Lind & Ponack

[57] ABSTRACT

A composition comprises a 1,7-disubstituted-4-oxo-3-quinolinecarboxylic acid or 1,7-disubstituted-4-oxo-3-naphthyridinecarboxylic acid derivative which is useful as a prophylactic and/or therapeutic agent for peripheral arterial obstruction, acute myocardial infarction, an antitumor agent, and as a prophylactic and/or therapeutic agent for osteoporosis.

8 Claims, No Drawings

QUINOLONECARBOXYLIC ACID DERIVATIVES, THEIR PRODUCTION AND USE

This is a divisional application of Ser. No. 08/207,091, filed Mar. 8, 1994 now U.S. Pat. No. 5,519,024.

The present invention relates to an animal cell adhesion inhibitory composition which comprises a 4-oxo-3-quinolinecarboxylic acid or 4-oxo-3-naphthyridinecarboxylic acid derivative possessing cell adhesion inhibitory activity, a novel 4-oxo-3-quinolinecarboxylic acid derivative and a method of production thereof.

The present invention is generally directed to the regulation or inhibition of cell adhesion to provide a therapeutic agent for various diseases.

Factors associated with animal cell adhesion to extracellular substrates include fibronectin, vitronectin, osteopontin, collagen, thrombospondin, fibrinogen and the von Willebrand factor. These proteins contain the tripeptide -Arg-Gly-Asp- as a cell recognition site. This tripeptide is recognized by at least one protein belonging to the category of receptor integrin, a hetero-dimer protein consisting of two membrane-bound subunits [E. Ruoslahti and M. D. Pierschbacher, Science, 238, 491 (1987)].

Structurally related integrin receptors which recognize the amino acid sequence -Arg-Gly-Asp- are known to be expressed in platelet extracellular surface glycoprotein GPIIb/IIIa, endothelial cells, leukocytes, lymphocytes, monocytes and granulocyte. Any compound having the amino acid sequence -Arg-Gly-Asp- competitively binds to cell adhesion factor adherent site to inhibit the binding of the cell adhesion factor. Such cell adhesion inhibitors include H-Gly-Arg-Gly-Asp-Ser-Pro-OH (SEQ ID NO:1).

Upon vascular vessel damage, platelets are activated by vascular endothelial collagen etc., resulting in fibrinogen binding thereto, i.e., platelet aggregation, leading to thrombosis. The platelet-fibrinogen interaction is mediated by GPIIb/IIIa, an important aspect of platelet aggregation. Cell adhesion inhibitors are capable of inhibiting platelet aggregation caused by platelet aggregation inducers, such as thrombin, epinephrine, ADP and collagen.

Also, cell adhesion inhibitors are expected to serve as drugs to suppress cancerous cell metastasis (inhibition of adhesive fixation at metastatic site).

Conventional cell adhesion inhibitors include linear or cyclic peptides containing the amino acid sequence -Arg-Gly-Asp- [e.g., Journal of Biochemistry, 262, 17294 (1987); Japanese Patent Unexamined Publication No. 174797/1990].

On the other hand, some quinolonecarboxylic acid compounds are commercially available as useful antimicrobial agents, but their cell adhesion inhibitory action is unknown.

Japanese Patent Unexamined Publication No. 251667/1986 describes that a benzoheterocyclic compound of the following formula or a salt thereof possesses an antibacterial activity, but discloses no cell adhesion inhibitory activity.

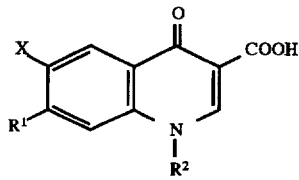

wherein $R^1$ is a halogen, a group

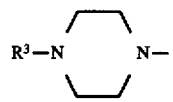

($R^3$ is H or a lower alkyl group) or 1-pyrrolidyl which may have amino, a lower alkylamino or an amino-lower alkyl as a substitutuent on thienyl ring); $R^2$ is thienyl which may have a halogen or a lower alkyl as a substituent on thienyl ring, thiazolyl, pyridyl which may have oxo as a substituent on pyridyl ring, pyrrolyl, furyl-lower alkyl, pyridyl-lower alkyl or morpholino; and X is a halogen.

Also, WO93/13091 describes that a quinolone derivative represented by the following formula (1) or a salt thereof possesses an antibacterial activity, but discloses no cell adhesion inhibitory activity.

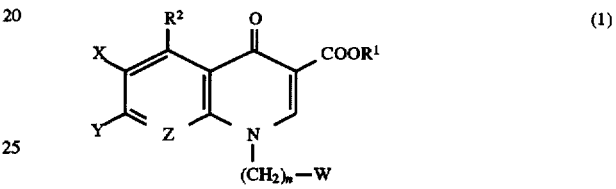

(1)

wherein $R^1$ represents hydrogen or a protective group; $R^2$ represents hydrogen, halogen or lower alkyl; X represents hydrogen or halogen; Y represents halogen, optionally substituted cyclic amino, optionally substituted lower cycloalkenyl, or $R^3$—$(CH_2)_m$—A— wherein $R^3$ represents hydrogen or optionally substituted amino, A represents oxygen or sulfur, and m represents a number of 0 to 3; Z represents nitrogen or C—$R^4$ wherein $R^4$ represents hydrogen or halogen; W represents an optionally substituted five-membered heterocyclic group having three or more heteroatoms among which at least two are nitrogen; and n represents a number of 0 to 2.

Further, U.S. Pat. No. 5,258,510 corresponding to Japanese Patent Unexamined Publication No. 154765/1992 describes a benzoheterocyclic compound represented by the following formula that possesses vasopressin antagonistic activity and serves well as a platelet agglutination inhibitor etc., but discloses no cell adhesion inhibitory activity.

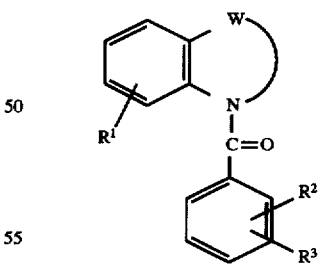

wherein $R^1$ represents a hydrogen atom, a halogen atom or the like; $R^2$ represents a hydrogen atom, a halogen atom or the like; $R^3$ represents a group

or the like; $R^4$ represents a hydrogen atom or the like; $R^5$ represents a group

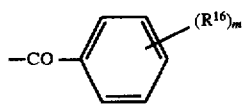

($R^{16}$ represents a halogen atom or the like; m represents 0 to 3); W represents a group $-(CH_2)_p-$ (p represents an integer from 3 to 5) or a group $-CH=CH-(CH_2)_q-$ (q represents 1 to 3), and each of the groups $-(CH_2)_p-$ and $-CH=CH-(CH_2)_q-$ may be substituted with a carboxyl group, an oxo group or another substituent.

Conventional peptide derivatives of cell adhesion inhibitors are not sufficiently potent, nor do they meet the requirement of oral absorbability. In addition, these peptide derivatives undergo hydrolysis by enzymes such as aminopeptidase, carboxypeptidase and various endopeptidases, e.g., serine protease, so that they lack stability in solutions and living bodies where such enzymes are present. With this feature, they are not satisfactory for pharmaceutical use. Accordingly, there is a need for the development of a cell adhesion inhibitor satisfactory for pharmaceutical use.

In an attempt to solve the above problems, the present inventors investigated in search for a new non-peptide cell adhesion inhibitor, and found that a compound having 4-oxo-3-quinolinecarboxylic acid or 4-oxo-3-naphthyridinecarboxylic acid with substituents at 1- and 7-positions as the base structure exhibits cell adhesion inhibiting action, an unexpected action totally different from antimicrobial or vasopressin antagonizing action, irrespective of types of 1- and 7-substituents and presence or absence or kind of substituents at other positions. The inventors made further investigation based on this finding, and developed the present invention.

Accordingly, the present invention relates to:

(1) a cell adhesion inhibitory composition which comprises a 1,7-disubstituted-4-oxo-3-quinolinecarboxylic acid or 1,7-disubstituted-4-oxo-3-naphthyridinecarboxylic acid derivative, (2) a cell adhesion inhibitory composition as described above in (1) which comprises a compound of the formula:

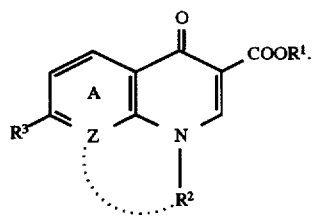

wherein Z is CH or N; $R^1$ is hydrogen or a carboxyl protecting group; $R^2$ is an organic group or may bind together with the carbon atom of the group CH for Z to form an optionally substituted 5- to 7-membered ring which may contain nitrogen, oxygen and/or sulfur atom(s); $R^3$ is an organic group; and ring A is optionally further substituted, or a salt thereof, (3) a cell adhesion inhibitory composition as described above in (1), which comprises a compound of the formula:

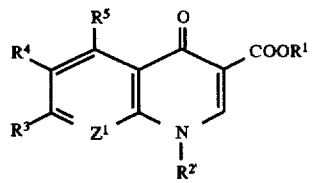

wherein $Z^1$ is CX where X is a halogen atom, cyano, a lower alkyl group, a lower alkoxy group or a lower alkylthio group or N; $R^{2'}$ is an organic group; $R^4$ is hydrogen or a halogen atom; $R^5$ is hydrogen, a halogen atom, a lower alkoxy group, amino or a lower alkylamino group; and the other symbols have the same definitions as above, or a salt thereof, (4) a compound of the formula:

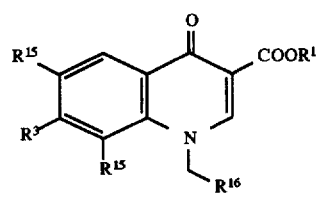

wherein $R^{14}$ and $R^{15}$ are hydrogen or a halogen atom; and $R^{16}$ is an optionally substituted 2-thiazolyl group; and the other symbols are as defined above or a salt thereof, (5) a compound of the formula:

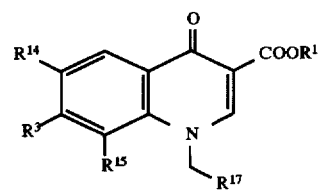

wherein $R^{17}$ is an optionally substituted phenyl group; and the other symbols are as defined above or a salt thereof, (6) a method for producing a compound (IV) or a salt thereof, which comprises reacting a compound of the formula:

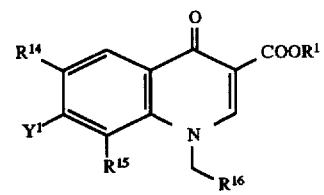

wherein $Y^1$ is a halogen atom and the other symbols are as defined above or a salt thereof with a compound of the formula $R^3-H$ (III)

wherein $R^3$ is as defined above or a salt thereof, (7) a method for producing a compound (V) or a salt thereof, which comprises reacting a compound of the formula:

(VII)

[Structure: quinolone with R14, Y1, R15 on benzene ring, COOR1 at 3-position, N-R17, ketone at 4-position]

wherein each symbol is as defined above or a salt thereof with a compound (III) or a salt thereof, etc.

In the above formulas, Z represents CH or N; $R^1$ represents hydrogen or a carboxyl protecting group.

The carboxyl protecting group for $R^1$ is a carboxylic acid ester residue which cleaves relatively easily to form the corresponding free carboxyl group.

This carboxyl protecting group is exemplified by ester-forming protecting groups such as $C_{1-6}$ alkyl groups (e.g., methyl, ethyl, methoxymethyl, methoxyethoxymethyl, benzyloxymethyl, tert-butyl, benzyl, p-methoxybenzyl, p-nitrobenzyl, o-nitrobenzyl, benzhydryl, trityl, 2,2,2-trichloroethyl, 2-trimethylsilylethyl) or $C_{2-6}$ alkenyl groups (e.g., allyl) which may be substituted with 1 to 3 substituents selected from the group consisting of a $C_{1-4}$ alkoxy group, benzyloxy, phenyl, nitro, a halogen atoms and silyl; and protecting groups which form a silyl ester such as $C_{1-6}$ alkylsilyl ester, phenylsilyl ester (e.g., trimethylsilyl, triethylsilyl, tert-butyldimethylsilyl, isopropyldimethylsilyl and dimethylphenylsilyl).

Other preferable examples of carboxyl protecting groups are those which form an ester which acts as a prodrug in vivo, including substituted $C_{1-4}$ alkyl groups such as 3-phthalidyl, (2-oxo-5-methyl-1,3-dioxolen-4-yl)methyl, acetoxymethyl, 1-acetoxyethyl, pivaloyloxymethyl, isopropoxycarbonyloxymethyl, 1-isopropoxycarbonyloxyethyl, 1-cyclopentyloxycarbonyloxyethyl and 1-cyclohexyloxycarbonyloxyethyl.

With respect to the above formulas, $R^2$ represents an organic group and may bind together with the carbon atom of the group CH for Z to form a 5- to 7-membered ring which may contain nitrogen, oxygen and/or sulfur atom(s) and which may be substituted. The organic group for $R^2$ is exemplified by an optionally substituted hydrocarbon, heterocyclic, alkoxy and amino group.

The hydrocarbon group as the organic group for $R^2$ is exemplified by lower alkyl groups, lower alkenyl groups, lower alkynyl groups, cycloalkyl groups which may be condensed with a benzene ring, cycloalkenyl groups, aryl groups and aralkyl groups.

The heterocyclic group as the organic group for $R^2$ and other heterocyclic groups mentioned in the present specification are non-aromatic heterocyclic groups or aromatic heterocyclic groups.

Preferable non-aromatic heterocyclic groups include 4- to 6-membered non-aromatic heterocyclic groups containing 1 to 3 hetero atoms selected from a nitrogen atom, an oxygen atom and a sulfur atom, such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl.

Preferable aromatic heterocyclic groups include 5- to 6-membered aromatic monocyclic heterocyclic groups containing 1 to 4 hetero atoms selected from a nitrogen atom, an oxygen atom and a sulfur atom such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and di- or tri-cyclic aromatic condensed heterocyclic groups containing 1 to 5 hetero atoms selected from a nitrogen atom, an oxygen atom and a sulfur atom, condensed with 1 or 2 benzene rings or 5- to 6-membered aromatic heterocyclic groups containing 1 to 4 hetero atoms selected from a nitrogen atom, an oxygen atoms and a sulfur atom, such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl.

The alkoxy group as the organic group for $R^2$ is exemplified by lower alkoxy groups such as methoxy, ethoxy, n-propoxy, isopropoxy, n-butoxy, isobutoxy, sec-butoxy, tert-butoxy, pentyloxy, isopentyloxy, tert-pentyloxy, neopentyloxy, hexyloxy, isohexyloxy, 1,1-dimethylbutoxy, 2,2-dimethylbutoxy and 3,3-dimethylbutoxy, with preference given to methoxy, ethoxy, propoxy, isopropoxy, n-butoxy, isobutoxy and the like.

The hydrocarbon or heterocyclic group as the organic group for $R^2$ may have one or more, preferably 1 to 3 appropriate substituents exemplified by lower alkyl groups, lower alkenyl groups, lower alkynyl groups, cycloalkyl groups which may be condensed with a benzene ring, aryl groups, heterocyclic groups, aralkyl groups, amino, N-monosubstituted amino groups, N,N-disubstituted amino groups, 4- to 7-membered cyclic amino groups, amidino, guanidino, acyl groups, carbamoyl, N-monosubstituted carbamoyl groups, N,N-disubstituted carbamoyl groups, sulfamoyl, N-monosubstituted sulfamoyl groups, N,N-disubstituted sulfamoyl groups, carboxyl, lower alkoxycarbonyl groups, hydroxyl, lower alkoxy groups, lower alkenyloxy groups, cycloalkyloxy groups, aralkyloxy groups, aryloxy groups, mercapto, lower alkylthio groups, aralkylthio groups, arylthio groups, sulfo, cyano, azide, nitro, nitroso and halogen atoms.

The alkoxy group or amino group as the organic group for $R^2$ may be substituted with 1 or 2 substituents selected from the group consisting of lower alkyl groups, lower alkenyl groups, cycloalkyl groups which may be condensed with a benzene ring, aryl groups, aralkyl groups, acyl groups, the heterocyclic groups specified above for the organic group for $R^2$ and the like.

Also, $R^2$ may bind together with the carbon atom of the group CH for Z, to form an optionally substituted 5- to 7-membered ring which may contain nitrogen, oxygen and/or sulfur atom(s). The 5- to 7-membered ring is exemplified by the following:

[Three ring structures shown: 5-, 6-, and 7-membered N-containing rings]

-continued

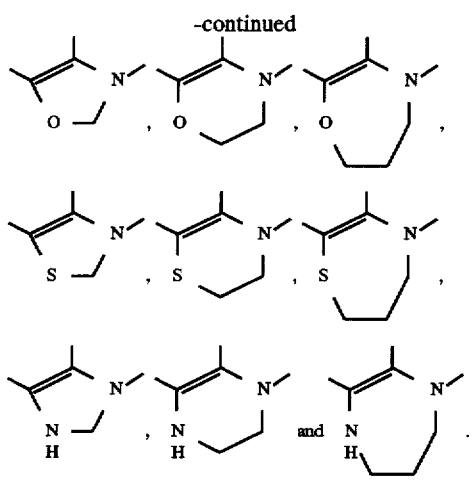

This 5- to 7-membered ring may be substituted with 1 or 2 of the same substituents as those specified above for the hydrocarbon or heterocyclic group as the organic group for $R^2$.

The organic group for $R^2$ is preferably exemplified by the group represented by the formula:

$$-(CH_2)_n-R^6$$

wherein $R^6$ is a phenyl group which may be substituted or a 5- or 6-membered aromatic heterocyclic group which may be substituted; and n represents an integer from 1 to 3.

The 5- or 6-membered aromatic heterocyclic group for $R^6$ is preferably an aromatic heterocyclic group having 1 to 3 hetero atoms selected from a nitrogen atom, an oxygen atom and a sulfur atom, exemplified by furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl and pyrazinyl, with preference given to thiazolyl and the like.

Substituents on the phenyl group or 5- or 6-membered aromatic heterocyclic group for $R^6$ include lower alkyl groups, halogen atoms, hydroxy, carboxyl, amino, mono- or di-lower alkylamino groups, 4- to 7-membered cyclic amino groups, lower alkoxy groups, lower alkylcarbonyloxy groups and cyano, the number of substituents being preferably 1 to 5, more preferably 1 to 3.

With respect to the above formulas, $R^3$ represents an organic group. Any organic group used as the 7-position substituent for quinolonecarboxylic acid series antimicrobial agents can be used as the organic group for $R^3$ without limitation, as long as the desired effect is achieved, with general preference given to organic groups having a nitrogen atom (basic groups). For example, the following groups ① to ⑤ are used.

① Optionally substituted amino groups represented by the formula:

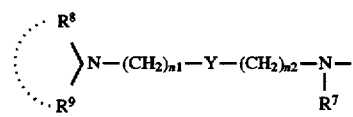

wherein $R^7$ is hydrogen or a lower alkyl group which may be substituted; $R^8$ and $R^9$ is hydrogen, a lower alkyl group which may be substituted or a lower alkenyl group which may be substituted or $R^8$ and $R^9$ may bind together with the adjacent nitrogen atom to form a nitrogen-containing heterocyclic group which may be substituted; Y is a straight or branched $C_{2-8}$ alkylene group, a cycloalkylene group, a cycloalkenylene group, an aromatic hydrocarbon group or a heterocyclic group; $n^1$ and $n^2$ is a whole number from 0 to 3.

The lower alkyl group for $R^7$, the lower alkyl group or lower alkenyl group for $R^8$ or $R^9$, and the nitrogen-containing heterocyclic group formed by $R^8$ and $R^9$ in cooperation with the adjacent nitrogen atom may be substituted with 1 to 3 of the same substituents specified above for the hydrocarbon group or heterocyclic group as the organic group for $R^2$.

The nitrogen-containing heterocyclic group formed by $R^8$ and $R^9$ in cooperation with the adjacent nitrogen atom is exemplified by the same nitrogen-containing groups specified above for the heterocyclic group as the organic group for $R^2$.

The straight or branched $C_{2-8}$ alkylene group for Y is exemplified by ethylene and propylene, etc.

The cycloalkylene group for Y is exemplified by $C_{3-7}$ cycloalkylene groups such as cyclobutylene and cyclobutyrene, etc.

The cycloalkenylene group for Y is exemplified by $C_{3-7}$ cycloalkenylene groups such as cyclopropenylene and cyclobutenylene, etc.

The aromatic hydrocarbon group for Y is exemplified by phenylene, etc.

The heterocyclic group for Y is exemplified by groups resulting from elimination of one hydrogen atom from the heterocyclic group specified as the organic group for $R^2$.

The optionally substituted amino group represented by formula [A] is exemplified by 2-aminoethylamino, 3-aminopropylamino, 4-aminobutylamino, 5-aminopentylamino, N-(2-aminoethyl)-N-methylamino, N-(2-aminoethyl)-N-ethylamino, N-(3-aminopropyl)-N-methylamino, N-(3-aminopropyl)-N-ethylamino, N-(4-aminobutyl)-N-methylamino, 2-(N-methylamino) ethylamino, 3-(N-methylamino)propylamino, 4-(N-methylamino)butylamino, 5-(N-methylamino)pentylamino, N-(2-methylaminoethyl)-N-methylamino, N-(3-methylaminopropyl)-N-methylamino, N-(4-methylaminobutyl)-N-methylamino, 2-(N-cyclopropylamino)ethylamino, 3-(N-cyclopropylamino) propylamino, 4-(N-cyclopropylamino)butylamino, N-(2-cyclopropylaminoethyl)-N-methylamino, N-(3-cyclopropylaminopropyl)-N-methylamino, 2-(N,N-dimethylamino)ethylamino, 3-(N,N-dimethylamino) propylamino, 4-(N,N-dimethylamino)butylamino, N-(2-dimethylaminoethyl)-N-methylamino, N-(3-dimethylaminopropyl)-N-methylamino, dimethylaminobutyl)-N-methylamino, N-(5-dimethylaminopentyl)-N-methylamino, 2-(pyrrolidino) ethylamino, 3-(pyrrolidino)propylamino, 4-(pyrrolidino) butylamino, 5-(pyrrolidino)pentylamino, 2-(piperizino) ethylamino, 3-(piperizino)propylamino, 4(piperizino) butylamino, 5-(piperizino)pentylamino, 2-(morpholino) ethylamino, 3-(morpholino)propylamino, 4-(morpholino) butylamino, 5-(morpholino)pentylamino, 2-(piperazin-1-yl) ethylamino, 3-(piperazin-1-yl)propylamino, 4-(piperazin-1-yl)butylamino, 5-(piperazin-1-yl)pentylamino, 2-(4-methylpiperazin-1-yl)ethylamino, 3-(4-methylpiperazin-1-yl)propylamino, 4-(4-methylpiperazin-1-yl)butylamino, 1,2-diaminocyclopentane, 1,3-diaminocyclopentane, 1-amino-2-methylaminocyclopentane, 1-amino-2-dimethylaminocyclopentane, 1,2-diaminocyclohexane, 1,3-diaminocyclohexane, 1,4-diaminocyclohexane, 1-amino-2-methylaminocyclohexane, 1-amino-3- methylaminocyclohexane, 1-amino-4-methylaminocyclohexane, 1-amino-2-dimethylaminocyclohexane, 1-amino-3-dimethylaminocyclohexane, 1-amino-4-dimethylaminocyclohexane and 1-amino-2-aminomethylcyclohexane, etc.

With respect to the formula [A],

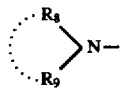

may be an amidino group

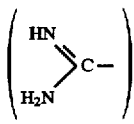

or a guanidino group

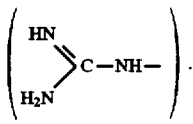

② Optionally substituted nitrogen-containing alkylthio groups represented by the formula:

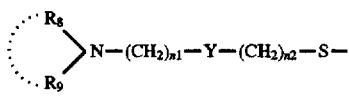  [B]

wherein the symbols have the same definitions as above.

Exemplified by 2-aminoethylthio, 3-aminopropylthio, 4-aminobutylthio, 5-aminopentylthio, 2-methylaminoethylthio, 3-methylaminopropylthio, 4-methylaminobutylthio, 5-methylaminopentylthio, 2-(dimethylamino)ethylthio, 3-(dimethylamino)propylthio, 4-(dimethylamino)butylthio, 5-(dimethylamino)pentylthio, 2-(piperazin-1-yl)ethylthio and 2-(4-methylpiperazin-1-yl)ethylthio, etc.

With respect to the formula [B],

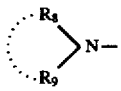

may be an amidino group or a guanidino group.

③ Optionally substituted nitrogen-containing alkoxy groups represented by the formula:

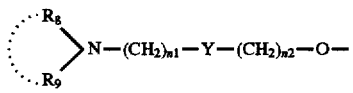  [C]

wherein the symbols have the same definitions as above.

Exemplified by 2-aminoethoxy, 3-aminopropoxy, 4-aminobutoxy, 5-aminopentyloxy, 2-methylaminoethylthio, 3-methylaminopropylthio, 4-methylaminobutylthio, 5-methylaminopentylthio, 2-(dimethylamino)ethylthio, 3-(dimethylamino)propylthio, 4-(dimethylamino)butylthio, 2-(piperazin-1-yl)ethylthio and 2-(4-methylpiperazin-1-yl)ethylthio, etc.

With respect to the formula [C],

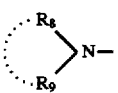

may be an amidino group or a guanidino group.

④ Optionally substituted cyclic amino groups represented by the formulas D1 through D19:

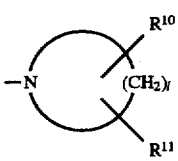 D1

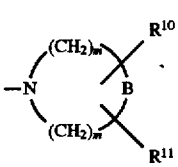 D2

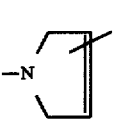 D3

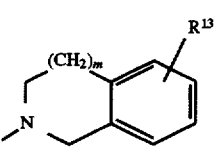 D4

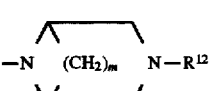 D5

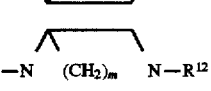 D6

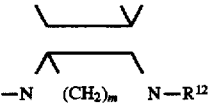 D7

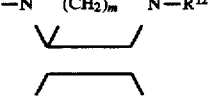 D8

 D9

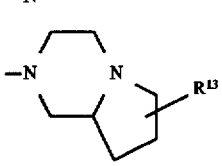 D10

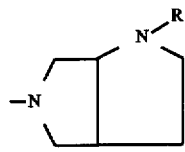
D11

D12

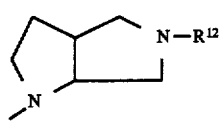
D13

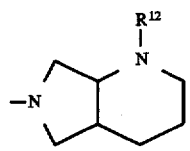
D14

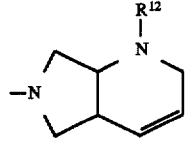
D15

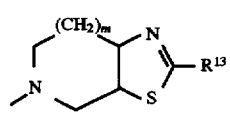
D16

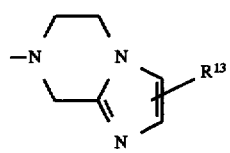
D17

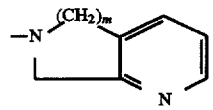
D18

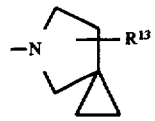
D19

With respect to the formula D1, l represents an integer from 2 to 6; $R^{10}$ and $R^{11}$ is hydrogen, hydroxyl, amino, a halogen atom, a lower alkyl group, a cycloalkyl group, a lower alkoxy group, a N-mono- or N,N-disubstituted amino group, a cycloalkylamino group, 4- to 7-membered cyclic amino group, a N-mono- or N,N-disubstituted amino-lower alkyl group, a N-mono- or N,N-disubstituted amino-lower alkoxy group, amidino, guanidino, an amidino-lower alkyl group, a guanidino-lower alkyl group, an amidino-lower alkoxy group, a guanidino-lower alkoxy group, an acyloxy group which may be substituted, a carbamoyloxy group which may be substituted, an acylamino group which may be substituted, an acylamino-lower alkyl group which may be substituted or an aryl group which may be substituted. These substituents may be present on the same atom or different atoms in the cyclic amino group represented by formula D1. The cyclic amino group represented by formula D1 is exemplified by azetidinyl group, pyrrolidinyl group, piperidinyl group, etc.

With respect to the formula D2, B represents an oxygen atom, a sulfur atom,

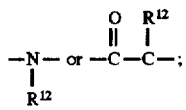

$R^{12}$ represents hydrogen atom, a lower alkyl group which may be substituted, a cycloalkyl group which may be substituted, an aryl group which may be substituted, a heterocyclic group which may be substituted, an acyl group which may be substituted or a lower alkoxycarbonyl group which may be substituted; m is 1 or 2 and m' is an integer from 1 to 3; the other symbols have the same definitions as above. The group of the formula D2 is exemplified by the piperazinyl group, homopiperazinyl group, morpholino group, thiomorpholino group, thiazolidinyl group, oxazolidinyl group and 3-oxo-1-piperazinyl group, etc.

With respect to the formulas D3, D4, D16 and D17, $R^{13}$ represents hydrogen, hydroxyl, amino, a halogen atom, a lower alkyl group, a cycloalkyl group, a lower alkoxy group, a N-mono- or N,N-disubstituted lower alkylamino group, a cycloalkylamino group, a N-mono- or N,N-disubstituted amino-lower alkyl group, a N-mono- or N,N-disubstituted amino-lower alkoxy group, amidino, guanidino, an amidino-lower alkyl group, a guanidino-lower alkyl group, an amidino-lower alkoxy group, a guanidino-lower alkoxy group, an acyloxy group which may be substituted, a carbamoyloxy group which may be substituted, an acylamino group which may be substituted, or an acylamino-lower alkyl group which may be substituted. With respect to the formulas D4–D18, $R^{12}$ and m is as defined above.

With respect to the above formulas, the acyloxy group, carbamoyloxy group, acylamino group, acylamino-lower alkyl group, aryl group, heterocyclic group, lower alkyl group, cycloalkyl group, acyl group and alkoxycarbonyl group represented by $R^{10}$, $R^{11}$, $R^{12}$ and $R^{13}$ may be substituted with 1 or 2 of the same substituents as those specified above for the hydrocarbon group or heterocyclic group as the organic group for $R^2$.

The heterocyclic group represented by the formula D5, D6, D7 or D8 is exemplified by the following:

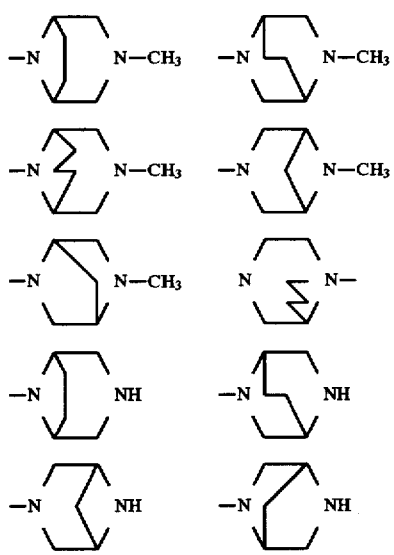

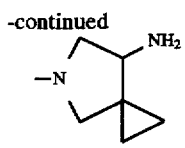

Preferable groups represented by the formulas D1 through D4 are as follows:

3-aminoazetidinyl group, 3-acetylaminoazetidinyl group, 3-methylaminoazetidinyl group, 3-dimethylaminoazetidinyl group, 3-aminomethylazetidinyl group, 3-aminoethylazetidinyl group, 3-amidinoethylazetiainyl group, 3-guanidinoethylazetidinyl group, pyrrolidinyl group, 3,4-dihydropyrrolidinyl group, 3-aminopyrrolidinyl group, 3-methylaminopyrrolidinyl group, 3-dimethylaminopyrrolidinyl group, 3-ethylaminopyrrolidinyl group, 3-diethylaminopyrrolidinyl group, 3-acetylaminopyrrolidinyl group, 3-aminomethylpyrrolidinyl group, 3-methylaminomethylpyrrolidinyl group, 3-dimethylaminomethylpyrrolidinyl group, 3-ethylaminomethylpyrrolidinyl group, 3-diethylaminomethylpyrrolidinyl group, 3-(1-aminoethyl)pyrrolidinyl group, 3-(2-aminoethyl)pyrrolidinyl group, 3-(1-amino-1-methylethyl)pyrrolidinyl group, 3-(1-methylaminoethyl)pyrrolidinyl group, 3-(1-dimethylaminoethyl)pyrrolidinyl group, 3-amino-5-methylpyrrolidinyl group, 3-amino-5-methylpyrrolidinyl group, 3-methylamino-4-methylpyrrolidinyl group, 3-dimethylamino-4-methylpyrrolidinyl group, 3-ethylamino-4-methylpyrrolidinyl group, 3-diethylamino-4-methylpyrrolidinyl group, 3-methylaminomethyl-4-methylpyrrolidinyl group, 3-ethylaminomethyl-4-methylpyrrolidirxyl group, 3-dimethylaminomethyl-4-methylpyrrolidinyl group, 3-amino-4-methoxypyrrolidinyl group, 3-methylamino-4-methoxypyrrolidinyl group, 3-dimethylamino-4-methoxypyrrolidinyl group, 3-amino-4-fluoropyrrolidinyl group, 3-amino-4-fluoromethylpyrrolidinyl group, 3-(2-aminoethoxy)pyrrolidinyl group, 3-(2-methylaminoethoxy)pyrrolidinyl group, 3-(2-dimethylaminoethoxy)pyrrolidinyl group, 3-(3-aminopropoxy)pyrrolidinyl group, 3-(3-methylaminopropoxy)pyrrolidinyl group, 3-(3-dimethylaminopropoxy)pyrrolidinyl group, 3-[(2-dimethylaminoethylamino)carbonyloxy]pyrrolidinyl group, 3-[(piperazin-1-yl)carbonyloxy]pyrrolidinyl group, 3-[(4-methylpiperazin-1-yl)carbonyloxy]pyrrolidinyl group, 3-aminopiperidino group, 4-aminopiperidino group, 3-methylaminopiperidino group, 4-methylaminopiperidino group, 3-dimethylaminopiperidino group, 4-dimethylaminopiperidino group, 3-methylaminomethylpiperidino group, 4-methylaminomethylpiperidino group, 3-dimethylaminomethylpiperidino group, 4-dimethylaminomethylpiperidino group, 3-(2-dimethylaminoethoxy)piperidino group, 4-(2-dimethylaminoethoxy)piperidino group, piperazinyl group, 4-methylpiperazinyl group, 3-methylpiperazinyl group, 4-acetylpiperazinyl group, 4-(aminoethyl)piperazinyl group, 4-(2-methylaminoethyl)piperazinyl group, 4-(2-dimethylaminoethyl)piperazinyl group, 4-(4-pyrridyl)piperazinyl group, 4-(3-pyridyl)piperazinyl group, 4-(2-pyridyl)piperazinyl group, 4-(4-pyridylmethyl)piperazinyl group, 4-(3-pyridylmethyl)piperazinyl group, 4-(2-pyridylmethyl)piperazinyl group, homopiperazinyl group, 4-methylhomopiperazinyl group, 3-aminomethylmorpholino group, 3-methylaminomethylmorpholino group, 3-dimethylaminomethylmorpholino group, 1,2,3,4-tetrahydroisoquinolin-2-yl group, 4-amino-1,2,3,4-tetrahydroisoquinolin-2-yl group, 4-aminomethyl-1,2,3,4-tetrahydroisoquinolin-2-yl group, 3-aminomethyl-3-pyrrolin-1-yl group, 3-methylaminomethyl-3-pyrrolin-1-yl group, 3-dimethylaminomethyl-3-pyrrolin-1-yl group and 2-aminomethylisoindolin-1-yl group, etc.

⑤ Amino, thiol or hydroxyl groups substituted with a 4- to 7-membered cyclic amine Exemplified by 4-piperidinylamino, 4-piperidinylthio and 4-piperidinyloxy, etc.

With respect to the above formula (I), ring A is an optionally further substituted benzene or pyridine ring. Although said substituent(s) on the benzene or piridine ring is not subject to limitation, the 5-position substituent on the quinoline ring or naphthyridine ring is preferably a halogen atom, a lower alkoxy group, an amino group, a lower alkylamino group or the like; the 6-position substituent is preferably a halogen atom or the like; the 8-position substituent is preferably a halogen atom, cyano, a lower alkyl group, a lower alkoxy group, a lower alkylthio group or the like.

In short, a compound (I) or a salt thereof includes preferably a compound of the formula:

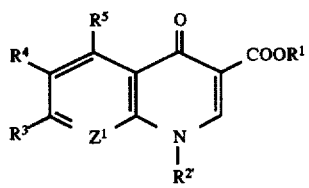

wherein $Z^1$ is CX (X is a halogen atom, cyano, a lower alkyl group, a lower alkoxy group or a lower alkylthio group) or N; $R^{2'}$ is an organic group; $R^4$ is hydrogen or a halogen atom; $R^5$ is hydrogen, a halogen atom, a lower alkoxy group, amino or a mono- or di-lower alkylamino group; the other symbols have the same definitions as above, or a salt thereof.

The organic groups for $R^{2'}$ is exemplified by the same organic groups as those mentioned for the above $R^2$.

And, among the compound (I) or a salt thereof, a compound of the formula

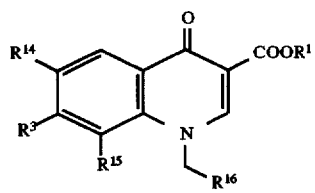

wherein $R^{14}$ and $R^{15}$ are hydrogen or a halogen atom; $R^{16}$ is an optionally substituted 2-thiazolyl group; and the other symbols are as defined above or a salt thereof and a compound of the formula:

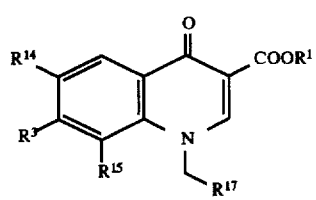

wherein $R^{17}$ is an optionally substituted phenyl group and the other symbols are as defined above or a salt thereof are novel.

While, in the formulas (IV) and (V), as organic groups shown by $R^3$, the same ones as shown by $R^3$ in the formula (I) are employed, preferable ones include 4-(4-pyridyl)piperazin-1-yl group; 4-(4-piperidinyl)piperidin-1-yl group; or a group represented by the formula:

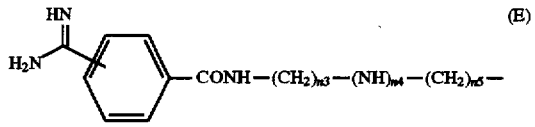

wherein $n^3$ is an integer of 0 to 4; $n^4$ is 0 or 1; and $n^5$ is a whole number 0 to 3. Especially, 4-(4-pyridyl)piperazin-1-yl group or 4-(4-piperidinyl)piperidin-1-yl group and the like is preferable.

As substituents of the 2-thiazolyl group for $R^{16}$ and the phenyl group for $R^{17}$, use is made of, for example, hydroxyl group, a lower alkoxyl group, a halogen atom and trifluoromethyl, the number of such substituents being preferably 1 to 3.

Among the groups represented by the formula (E), while amidino group may be substituted at any position on the benzene ring, those substituted at 3- or 4-position are preferable.

Preferable examples of the compound (IV) or a salt thereof include 7-[4-(4-pyridyl)piperazin-1-yl]-1-(2-thiazolylmethyl)-1,4-dihydro-4-oxoquinoline 3-carboxylic acid, 6,8-difluoro-7-[4-(4-pyridyl)piperazin-1-yl]-1-(2-thiazol-ylmethyl)-1,4-dihydro-4-oxoquinoline-3-carboxylic acid, 7-[4-(4-piperidinyl)piperidin-1-yl]-1-(2-thiazolylmethyl)-1,4-dihydro-4-oxoquinoline-3-carboxylic acid, 6,8-difluoro-7-[4-(4-piperidinyl)piperidin-1-yl]-1-(2-thiazolylmethyl)-1,4-dihydro-4-oxoquinoline-3-carboxylic acid, 7-(4-amidinobenzoyl)amino-1-(2-thiazolylmethyl)-1,4-dihydro-4-oxoquinoline-3-carboxylic acid, 7-(4-amidinobenzoyl)aminomethyl-1-(2-thiazolylmethyl)-1,4-dihydro-4-oxoquinoline-3-carboxylic acid, 7-[2-(4-amidinobenzoyl)amino]ethyl-1-(2-thiazolylmethyl)-1,4-dihydro-4-oxoquinoline-3-carboxylic acid, 7-[3-(4-amidinobenzoyl)amino]propyl-1-(2-thiazolylmethyl)-1,4-dihydro-4-oxoquinoline-3-carboxylic acid, 7-[4-(4-amidinobenzoyl)piperazin-1-yl]-1-(2-thiazolylmethyl)-1,4-dihydro-4-oxoquinoline-3-carboxylic acid, 7-[2-(4-amidinobenzoyl)amino]ethylamino-1(2-thiazolylmethyl)-1,4-dihydro-4-oxoquinoline-3-carboxylic acid or 7-[3-(4-amidinobenzoyl)amino]propylamino-1-(2-thiazolylmethyl)-1,4-dihydro-4-oxoquinoline 3-carboxylic acid and their salts, especially preferable ones being 6,8-difluoro-7-[4-(4-pyridyl)piperazin-1-yl]-1-(2-thiazolylmethyl)-1,4-dihydro-4-oxoquinoline-3-carboxylic acid or 6,8-difluoro-7-[4-(4-piperidinyl)piperidin-1-yl]-1-(2-thiazolylmethyl)-1,4-dihydro-4-oxoquinoline-3-carboxylic acid or their salts.

Terms used in the present specification are defined as follows:

The lower alkyl group and the lower alkyl moiety in the lower alkylthio group, mono- or di-lower alkylamino group, N-mono- or N,N-di-substituted amino-lower alkyl group, amidino-lower alkyl group, guanidino-lower alkyl group or acylamino-lower alkyl group or lower alkylcarbonyloxy group are preferably exemplified by $C_{1-6}$ alkyl groups such as methyl, ethyl, n-propyl, isopropyl, n-butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl and 2-ethylbutyl, with preference given to methyl, ethyl, propyl, isopropyl, n-butyl and isobutyl, etc.

The lower alkenyl group and the lower alkenyl moiety in the lower alkenyloxy group are preferably exemplified by $C_{2-6}$ alkenyl groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl, with preference given to vinyl, allyl, isopropenyl and 2-methyl-1-propenyl, etc.

The lower alkynyl group is preferably exemplified by $C_{2-6}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl, with preference given to ethynyl, 1-propinyl and 2-propynyl, etc.

The cycloalkyl group and the cycloalkyl moiety in the cycloalkyloxy group or cycloalkylamino group is preferably exemplified by $C_{3-10}$ cycloalkyl groups such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl, etc.

The cycloalkyl group condensed with a benzene ring is preferably exemplified by $C_{4-7}$ cycloalkyl groups condensed with a benzene ring such as 1-indanyl and 2-indanyl.

The cycloalkenyl group is preferably exemplified by $C_{4-7}$ cycloalkenyl groups such as 2-cyclopenten-1-yl, 3-cyclopenten-1-yl, 2-cyclohexen-1-yl and 3-cyclohexen-1-yl.

The aryl group and the aryl moiety in the aryloxy group or arylthio group are monocyclic or condensed polycyclic aromatic hydrocarbon groups, with preference given to $C_{6-14}$ aryl groups such as phenyl, naphthyl, anthryl and phenanthryl, with more preference given to phenyl, 1-naphthyl and 2-naphthyl, etc.

The aralkyl group and the aralkyl moiety in the aralkyloxy group or aralkylthio group are exemplified by $C_{6-14}$ aryl-$C_{1-4}$ alkyl groups such as benzyl, phenethyl, 3-phenylpropyl, (1-naphthyl)methyl and (2-naphthyl)methyl, with preference given to benzyl and phenethyl, etc.

The N-monosubstituted amino group and the N-monosubstituted amino moiety in the N-monosubstituted amino-lower alkyl or -lower alkoxy group are an amino group having one substituent, which substituent is exemplified by lower alkyl groups, cycloalkyl groups, aryl groups, heterocyclic groups, aralkyl groups, amino, acyl groups, carbamoyl, lower alkoxycarbonyl groups, hydroxyl, lower alkoxy groups and aralkyloxy groups.

The N,N-disubstituted amino group and the N,N-disubstituted amino moiety in the N,N-disubstituted amino-lower alkyl or -lower alkoxy group are an amino group having two substituents, which substituents are exemplified by the same substituents as those specified above for the N-monosubstituted amino group on one hand and lower alkyl groups, cycloalkyl groups, aryl groups and aralkyl groups on the other hand.

The 4- to 7-membered cyclic amino group is preferably exemplified by the 1-azetidinyl group, 1-pyrrolidinyl group, piperidino group, morpholino group, 1-piperazinyl group and 1-piperazinyl groups having a lower alkyl, aralkyl, aryl group or the like at 4-position.

The acyl group and the acyl moiety in the acyloxy group, acylamino group or acylamino-lower alkyl group are exemplified by aliphatic acyl groups such as formyl group, alkanoyl groups, alkenoyl groups, cycloalkanecarbonyl groups and alkanesulfonyl groups, etc; aromatic acyl groups such as aroyl groups, arylalkanoyl groups, arylalkenoyl groups and arylsulfonyl groups, etc, heterocyclic aromatic acyl groups such as aromatic heterocyclic carbonyl groups and aromatic heterocyclic alkanoyl groups, etc.; and non-aromatic heterocyclic carbonyl groups (aliphatic heterocyclic carbonyl groups).

The alkanoyl group is an alkylcarbonyl group, preferably exemplified by $C_{1-6}$ alkyl-carbonyl groups such as acetyl, propionyl, butyryl, isobutyryl, valeryl, isovaleryl, pivaloyl and hexanoyl.

The alkenoyl group is an alkenylcarbonyl group, preferably exemplified by $C_{2-6}$ alkenyl-carbonyl groups such as acryloyl, methacryloyl, crotonoyl and isocrotonoyl.

The cycloalkanecarbonyl group is a cycloalkylcarbonyl group, preferably exemplified by $C_{4-7}$ cycloalkyl-carbonyl groups such as cyclopropanecarbonyl group, cyclobutanecarbonyl group, cyclopentanecarbonyl group and cyclohexanecarbonyl group.

The alkanesulfonyl group is an alkylsulfonyl group, preferably exemplified by $C_{1-6}$ alkyl-sulfonyl groups such as mesyl, ethanesulfonyl and propanesulfonyl.

The aroyl group is an arylcarbonyl group, preferably exemplified by $C_{6-14}$ aryl-carbonyl groups such as benzoyl, p-toluoyl, 1-naphthoyl and 2-naphthoyl.

The arylalkanoyl group is an alkylcarbonyl group substituted with an aryl group, preferably exemplified by $C_{6-14}$ aryl-$C_{1-6}$ alkyl-carbonyl groups such as phenylacetyl, phenylpropionyl, hydroatropoyl and phenylbutyryl.

The arylalkenoyl group is an alkenylcarbonyl group substituted with an aryl group, preferably exemplified by $C_{6-14}$-aryl-$C_{2-6}$ alkenylcarbonyl groups such as cinnamoyl and atropoyl.

The arylsulfonyl group is preferably exemplified by $C_{6-14}$ arylsulfonyl groups such as benzenesulfonyl and p-toluenesulfonyl.

Preferable aromatic heterocyclic-carbonyl groups include furoyl, thenoyl, nicotinoyl, isonicotinoyl, pyrrolcarbonyl, oxazolecarbonyl, thiazolecarbonyl, imidazolecarbonyl and pyrazolecarbonyl.

The aromatic heterocyclic-alkanoyl group is an alkylcarbonyl group substituted with an aromatic heterocyclic group as mentioned above, preferably exemplified by aromatic heterocyclic ring-$C_{1-6}$ alkyl-carbonyl groups such as thienylacetyl, thienylpropanoyl, furylacetyl, thiazolylacetyl, 1,2,4-thiadiazolylacetyl and pyridylacetyl.

Preferable non-aromatic heterocyclic-carbonyl groups include azetidinylcarbonyl, pyrrolidinylcarbonyl and pipedidinylcarbonyl, etc.

The N-monosubstituted carbamoyl group is a carbamoyl group having one substituent on the nitrogen atom, exemplified by the same substituents as those mentioned for the above mono-substituted amino group.

The N,N-disubstituted carbamoyl group is a carbamoyl group having two substituents on the nitrogen atom, exemplified by the same substituents as those specified above for the N-monosubstituted amino group on one hand and lower alkyl groups, cycloalkyl groups and aralkyl groups on the other hand. Also, the two substituents may bind together with the nitrogen atom to form a cyclic amino group. In such case, the N,N-disubstituted carbamoyl group is exemplified by 1-azetidinylcarbonyl, 1-pyrrolidinylcarbonyl, piperidinocarbonyl, morpholinocarbonyl, 1-piperazinylcarbonyl and 1-piperazinylcarbonyls having a lower alkyl, aralkyl, aryl group or the like at 4-position.

The N-monosubstituted sulfamoyl group is a sulfamoyl group having one substituent on the nitrogen atom, exemplified by lower alkyl groups, cycloalkyl groups, aryl groups, heterocyclic groups, aralkyl groups, amino groups, N-monosubstituted amino groups and N,N-disubstituted amino groups.

The N,N-disubstituted sulfarnoyl group is a sulfarnoyl group having two substituents on the nitrogen atom, exemplified by the same substituents as those specified above for the N-monosubstituted sulfamoyl group on one hand and lower alkyl groups, cycloalkyl groups and aralkyl groups on the other hand. Also, the two substituents may bind together with the nitrogen atom to form a cyclic amino group. In such case, the N,N-disubstituted sulfamoyl group is exemplified by 1-azetidinylsulfonyl, 1-pyrrolidinylsulfonyl, piperidinosulfonyl, morpholinosulfonyl, 1-piperazinylsulfonyl and 1-piperazinylsulfonyl having a lower alkyl, aralkyl, aryl group or the like at 4-position.

Preferable lower alkoxycarbonyl groups include $C_{1-6}$ alkoxy-carbonyl groups such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentylocycarbonyl and tert-pentyloxycarbonyl, with preference given to methoxycarbonyl, ethoxycarbonyl and propoxycarbonyl, etc.

The lower alkoxy group and the lower alkoxy moiety in the mono- or di-substituted amino-lower alkoxy group, amidino-lower alkoxy group or guanidino-lower alkoxy group are preferably exemplified by $C_{1-6}$ alkoxy groups such as methoxy, ethoxy, propoxy, isopropoxy, butoxy, isobutoxy, sec-butoxy, tert-butoxy, pentyloxy, isopentyloxy, tert-pentyloxy, neopentyloxy, hexyloxy, isohexyloxy, 1,1-dimethylbutoxy, 2,2-dimethylbutoxy and 3,3-dimethylbutoxy, with preference given to methoxy, ethoxy, propoxy, isopropoxy, butoxy and isobutoxy, etc.

Preferable halogen atoms include fluorine, chlorine, bromine and iodine, with preference given to fluorine, chlorine and bromine, with greater preference given to fluorine and chlorine.

The salt of the compound (I), (IV) or (V) includes a pharmaceutically acceptable salt, exemplified by salts with inorganic bases, salts with organic bases, salts with inorganic acids, salts with organic acids and salts with basic or acidic amino acids. Preferable salts with inorganic bases include alkali metal salts such as sodium salt and potassium salt, alkaline earth metal salts such as calcium salt and magnesium salt, aluminum salt and ammonium salt. Preferable salts with organic bases include salts with trimethylamine, triethylamine, pyridine, picoline, ethanolamine, diethanolamine, triethanolamine, dicyclohexylamine and N,N'-dibenzylethylenediamine. Preferable salts with inorganic acids include salts with hydrochloric acid, hydrobromic acid, nitric acid, sulfuric acid and phosphoric acid. Preferable salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable salts with basic amino acids include salts with arginine, lysine and ornithine. Preferable salts with acidic amino acids include salts with aspartic acid and glutamic acid.

The compound (I) or a salt thereof can occur as a hydrate. Such forms of the compound (I) or a salt thereof is included in the compounds of the present invention.

The compound (I) or a salt thereof may have asymmetric carbon; such forms of the compound (I) or a salt thereof can occur as optically active configurations. Such optical isomers are also included in the compounds of the present invention. The compound (I) or a salt thereof may have a number of asymmetric carbon atoms; such forms of the compound (I) or a salt thereof can occur as different stereomers, which are also included in the present invention.

The compound (I) or a salt thereof can be produced by a known method or modification thereof. Methods which can be used for this purpose include those described in German Patent Publication Nos. 3,142,854, 3,420,743, 3,318,145 and 3,409,922, European Patent Publication Nos. 113,091, 3,318,145, 47,005, 153,580, 131,839 and 154,780, and Japanese Patent Unexamined Publication Nos. 138582/1979 and 33453/1980 or a method analogous thereto.

Also, the compound (I) or a salt thereof can be produced by reacting a compound of the formula:

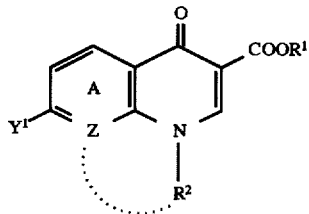

wherein $Y^1$ is a halogen atom, the other symbols are as defined above or a salt thereof with a compound of the formula:

$R^3$—H (III)

wherein the symbol is as defined above or a salt thereof.

The compound (IV) or (V) or its salts may be produced by a method analogous to the method described in J. Med. Chem. 23, 1358 (1980).

More specifically, the compound (IV) or a salt thereof can be produced by reacting a compound of the formula:

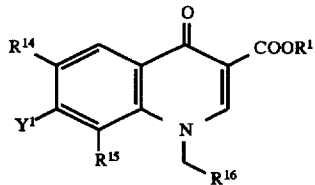

wherein each symbol is as defined above or a salt thereof with the compound (III) or a salt thereof.

Also, the compound (V) or a salt thereof can be produced by reacting a compound of the formula:

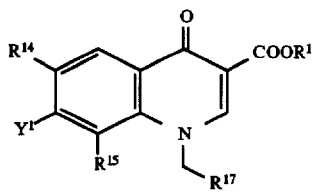

wherein each symbol is as defined above or a salt thereof with the compound (III) or a salt thereof.

The reaction of the compound (II), (VI) or (VII) or a salt thereof and the compound (III) or a salt thereof is carried out in an appropriate solvent in the presence of a basic compound.

Solvents which can be used here include alcohols such as methanol, ethanol and isopropanol, ketones such as acetone and methyl ethyl ketone, ethers such as dioxane, aromatic hydrocarbons such as benzene, toluene and xylene, amides such as dimethylformamide, dimethylacetamide and N-methylpyrrolidone, sulfoxides such as dimethyl sulfoxide, and pyridines such as pyridine and picoline.

Basic compounds which can be used here include inorganic bases such as alkali metal hydroxides, e.g., sodium hydroxide and potassium hydroxide, alkali metal carbonates, e.g., potassium carbonate and sodium carbonate, alkali metal hydrides, e.g., sodium hydride and potassium hydride, and alkali metal alkoxides, e.g., sodium methoxide and sodium ethoxide, and organic bases such as triethylamine and 1,8-diazabicyclo[5.4.0]undeca-7-ene.

The amount of the compound (III) or a salt thereof used is normally 1 to 5 mol, preferably 1 to 2 mol per mol of the compound (II), (VI) or (VII) or a salt thereof.

Reaction temperature is 15° to 200° C., preferably 80° to 120° C., or near the solvent's boiling point, reaction time being 1 to 24 hours.

In this reaction, a compound having a hydrogen atom for $R^1$ can be derived by ordinary hydrolysis, provided that $R^1$ is a carboxyl protecting group. This hydrolysis can be achieved under any set of ordinary hydrolysis conditions. Specifically, the reaction is carried out in a solvent selected from the group comprising water, alcohols such as methanol, ethanol and isopropanol, ketones such as acetone and methyl ethyl ketone, ethers such as dioxane, ethylene glycol and diethyl ether, acetic acid and mixtures thereof in the presence of a salt basic compound such as sodium hydroxide, potassium hydroxide, barium hydroxide or potassium carbonate or an acidic compound such as sulfuric acid, hydrochloric acid or acetic acid. The reaction proceeds at about 15° to 200° C., preferably about 15° to 150° C., reaction time being about 0.5 to 30 hours.

The salt of the compound (II), (III), (VI) or (VII) is exemplified by the same salts as those mentioned for the above compound (I), (IV) or (V).

In the present invention, the compound (II) or a salt thereof used as the starting compound can be produced by a known method or a method analogous thereto. Examples of the compound (II) obtained by a known method are given below.

7-chloro-1-cyclopropyl-6-fluoro-1,4-dihydro-4-oxo-3-quinolinecarboxylic acid (German Patent Publication No. 3,142,854), 1-cyclopropyl-6,7-difluoro-1,4-dihydro-4-oxo-3-quinolinecarboxylic acid (European Patent Publication No. 113,091), 6-chloro-1-cyclopropyl-7,8-difluoro-1,4-dihydro-4-oxo-3-quinolinecarboxylic acid (German Patent Publication No. 3,420,743), 8-chloro-1-cyclopropyl-6,7-difluoro-1,4-dihydro-4-oxo-3-quinolinecarboxylic acid (German Patent Publication No. 3,420,743), 1-cyclopropyl-6,7,8-trifluoro-1,4-dihydro-4-oxo-3-quinolinecarboxylic acid (Geman Patent Publication No. 3,318,145), 6,8-dichloro-1-cyclopropyl-7-fluoro-1,4-dihydro-4-oxo-3-quinolinecarboxylic acid (German Patent Publication No. 3,420,743), 1-cyclopropyl-6,7-difluoro-1,4-dihydro-8-methyl-4-oxo-3-quinolinecarboxylic acid, 1-cyclopropyl-7-chloro-6-fluoro-1,4-dihydro-8-nitro-4-oxo-3-quinolinecarboxylic acid, 6,7-difluoro-1-ethyl-1,4-dihydro-4-oxo-3-quinolinecarboxylic acid, 7-chloro-6-fluoro-1-ethyl-1,4-dihydro-4-oxo-3-quinolinecarboxylic acid, 7-chloro-6-fluoro-1,4-dihydro-1-(2-hydroxyethyl)-4-oxo-3-quinolinecarboxylic acid, 6,7-difluoro-1-(2-fluoroethyl)-1,4-dihydro-4-oxo-3-quinolinecarboxylic acid, 7-chloro-6-fluoro-1,4-dihydro-1-methoxy-4-oxo-3-quinolinecarboxylic acid, 7-chloro-6-fluoro-1,4-dihydro-1-methylamino-4-oxo-3-quinolinecarboxylic acid, 6,7-difluoro-1,4-dihydro-4-oxo-1-phenyl-3-quinolinecarboxylic acid, 7-chloro-1-cyclopropyl-6-fluoro-1,4-dihydro-4-oxo-1,8-naphthyridine-3-carboxylic acid, 6,7-dichloro-1-cyclopropyl-1,4-dihydro-4-oxo-1,8-n aphthyridine-3-carboxylic acid, 1-cyclopropyl-6,7,8-trihydro-1,4-dihydro-4-oxo-3-quinolinecarboxylic acid ethyl (European Patent Publication No. 3,318,145), 9,10-difluoro-2,3-dihydro-3-methyl-7-oxo-7H-pyrido[1,2,3-de][1,4]benzoxazin-6-carboxylic acid (European Patent Publication No. 47,005), 8,9-difluoro-6,7-dihydro-5-methyl-1-carboxylic acid, 7-chloro-6-fluoro-phenyl-1,4- dihydro-4-oxo-1,8-naphthyridine-3-carboxylic acid (European Patent Publication No. 153,580), 7-chloro-6-fluoro-1-(4-fluorophenyl)-1,4-dihydro-4-oxo-1,8-naphthyridine-3-carboxylic acid (European Patent Publication No. 153,580), 6,7,8-trifluoro-1,4-dihydro-1-methylamino-4-oxo-3-quinolinecarboxylic acid (German Patent Publication No. 3,409,922), 7-chloro-6-fluoro-1,4-dihydro-8-nitro-4-oxo-1-phenyl-3-quinolinecarboxylic acid, 7-chloro-6-fluoro-1-(4-fluorophenyl)-1,4-dihydro-8-nitro-4-oxo-3-quinolinecarboxylic acid, 6,7-difluoro-1-(4-fluorophenyl)-1,4-dihydro-8-methyl-4-oxo-3-quinolinecarboxylic acid, 6-chloro-7-fluoro-1-(4-fluorophenyl)-1,4-dihydro-4-oxo-3-quinolinecarboxylic acid (European Patent Publication No. 131,839), 6-chloro-7-fluoro-1-(2,4-difluorophenyl)-1,4-dihydro-4-oxo-3-quinolinecarboxylic acid (European Patent Publication No. 131,839), 6,7,8-trifluoro-1-(4-fluorophenyl)-1,4-dihydro-4-oxo-3-quinolinecarboxylic acid (European Patent Publication No. 154,780), 6,7,8-trifluoro-1-(2,4-difluorophenyl)-1,4-dihydro-4-oxo-3-quinolinecarboxylic acid (European Patent Publication No. 154,780), 6,7,8-trifluoro-1,4-dihydro-4-oxo-1-phenyl-3-quinolinecarboxylic acid (European Patent Publication No. 154,780), 7-chloro-1-ethyl-6-fluoro-1,4-dihydro-4-oxo-1,8-naphthyridine-3-carboxylic acid, 6,7-difluoro-1,4-dihydro-4-oxo-1-vinyl-3-quinolinecarboxylic acid, 1-cyclopropyl-5,6,7,8-tetrafluoro-1,4-dihydro-4-oxo-3-quinolinecarboxylic acid, 5-amino-1-cyclopropyl-6,7,8-trifluoro-1,4-dihydro-4-oxo-3-quinolinecarboxylic acid, 1-cyclopropyl-6,7,8-trifluoro-1,4-dihydro-5-hydroxy-4-oxo-3-quinolinecarboxylic acid, 1-cyclopropyl-6,7-difluoro-1,4-dihydro-8-methoxy-4-oxo-3-quinolinecarboxylic acid.

The compound (II) or (VII) or a salt thereof used as the starting compound can be produced by a known method, for example, the method described in J. Med. Chem., 11, 160 (1968), or J. Heterocyclic Chem., 22, 1022 (1985), or methods analogous thereto.

The cell adhesion inhibitory composition of the present invention may be used in the form of the compound (I) or a salt thereof as such, or may be mixed with a pharmacologically acceptable carrier.

Pharmacologically acceptable carriers are various organic or inorganic carrier substances in common use as pharmaceutical materials, including excipients, lubricants, binders and disintegrating agents, solvents, dissolution aids, suspending agents, isotonizing agents, buffers and soothing agents added as appropriate. Other pharmaceutical additives such as preservatives, antioxidants, coloring agents and sweetening agents may be used as necessary. Preferable excipients include lactose, sucrose, D-mannitol, starch, crystalline cellulose and light silicic anhydride. Preferable lubricants include magnesium stearate, calcium stearate, talc and colloidal silica. Preferable binders include crystalline cellulose, sucrose, D-mannitol, dextrin, hydroxypropyl cellulose, hydroxypropylmethyl cellulose and polyvinylpyrrolidone. Preferable disintegrating agents include starch, carboxymethyl cellulose, carboxymethyl cellulose calcium, crosscalmellose sodium and carboxymethyl starch sodium. Preferable solvents include water for injection, alcohol, propylene glycol, macrogol, sesame oil and corn oil. Preferable dissolution aids include polyethylene glycol, propylene glycol, D-mannitol, benzyl benzoate, ethanol, tris-aminomethane, cholesterol, triethanolamine, sodium carbonate and sodium citrate. Preferable suspending agents include surfactants such as stearyltriethanolamine, sodium lauryl sulfate, laurylaminopropionic acid, lecithin, benzalkonium chloride, benzethonium chloride and monostearic glycerol, and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include sodium chloride, glycerol and D-mannitol. Preferable buffers include buffer solutions of phosphates, acetates, carbonates and citrates. Preferable soothing agents include benzyl alcohol. Preferable preservatives include p-oxybenzoic acid esters, chlorobutanol, benzyl alcohol, phenethyl alcohol, dehydroacetic acid and sorbic acid. Preferable antioxidants include sulfites and ascorbic acid.

The cell adhesion inhibitory composition of the present invention can be used in various dosage forms such as tablets, lacquered tablets, sugar-coated tablets, hard or soft gelatin capsules, solutions, emulsions, suspensions, suppositories, sprays and injections.

To prepare tablets, lacquered tablets, sugar-coated tablets or hard gelatin capsules, the compound (I) or a salt thereof may be mixed with pharmaceutically inert inorganic or organic excipients such as lactose, corn starch or derivatives thereof, talc and stearic acid or salts thereof. Appropriate excipients for soft gelatin capsules include vegetable oils, waxes, fats, semi-solid and liquid polyols. However, as long as the nature of the compound (I) or a salt thereof permits, no excipients are necessary to prepare soft gelatin capsules.

To prepare solutions, emulsions, or suspensions, the compound (I) or a salt thereof may be mixed with appropriate excipients such as water, polyol, sucrose, invert sugar and glucose.

To prepare suppositories, the compound (I) or a salt thereof may be mixed with natural or artificially hardened oils, waxes, fats, semi-liquid of liquid polyols.

To prepare sprays, the compound (I) or a salt thereof may be mixed with spraying agents such as dimethyl ether.

To prepare injections, the compound (I) or a salt thereof may be mixed with water, alcohol, polyol, glycerol or vegetable oil.

These preparations can be produced by conventional methods using an appropriate mount (preferably about 10 to 100 w/w % relative to the preparation) of the compound (I) or a salt thereof.

The inventive preparation thus obtained is weakly toxic and exhibits various forms of cell adhesion inhibition such as inhibition of binding of fibrinogen, fibronectin and von Willebrand factor to platelet fibrinogen receptor (glycoprotein IIb/IIIa), and inhibition of binding of these and other sticky proteins such as vitronectin, collagen and laminin to receptors on the surface of various types of cells.

With these features, the cell adhesion inhibitory composition of the present invention affects cell-cell interaction and cell-matrix interaction, interfering with platelet thrombosis, in particular. The cell adhesion inhibitory composition of the present invention can therefore be used to treat or prevent peripheral arterial obstruction, acute myocardial infarction (AMI), deep venous thrombosis, pulmonary embolism, dissecting aneurysms, transient ischemic attack (TIA), cerebral stroke and other obstructive disorders, instable angina pectoris, diffuse intravascular clotting (DIC), sepsis, surgical or infectious shock, postoperative or postpartum traumas, plastic surgery for various arteries, cardiopulmonary and coronary bypass surgery, incompatible blood transfusion, early mazolysis, thrombotic thrombocytopenic purpura (TTP), asthma, acute or chronic renal diseases and diabetes mellitus, inflammations, arteriosclerosis, hemolytic uremic syndrome (HUS), symmetric peripheral necrosis, decubitus and organ graft rejection in mammals, including humans.

The cell adhesion inhibitory composition of the present invention can also be used to enhance the action of thrombolytic agents, to prevent re-obstruction after PTCR (percutaneous transluminal coronary reconstruction) or PTCA (percutaneous transluminal coronary angioplasty), to prevent thrombocytopenia due to dialysis, and to prevent heparin-induced thrombocytopenia and thrombosis by artificial blood vessels and organs. It can also be used as an antitumor agent to inhibit cancerous metastasis and as an anti-infection agent to prevent bacterial infiltration into organs.

The cell adhesion inhibitory composition of the present invention can be used in combination with antiplatelet drugs or anticoagulants such as heparin, aspirin and Warfarin. The cell adhesion inhibitory composition of the present invention also suppresses bone resorption by osteoclasts, and can be used to prevent or treat metabolic bone diseases such as osteoporosis.

The cell adhesion inhibitory composition of the present invention can be administered orally or non-orally, as a pharmaceutical composition in a dosage form as described above, to mammals (e.g., humans, rabbits, dogs, cats, rats, mice, guinea pigs). Although dose varies depending on subject of administration, target disease, symptom, route of administration and other factors, daily dose is about 0.1 to 20 mg/kg, preferably about 0.5 to 4 mg/kg as active ingredient for oral administration to an adult suffering from peripheral arterial obstruction. In non-oral administrations such as intravenous injection, daily dose is about 0.01 to 2.0 mg/kg, preferably about 0.05 to 0.4 mg/kg for an adult.

The present invention is hereinafter described in more detail by means of the following test example, reference example, production examples and working examples, which examples are not to be construed as limitative.

TEST EXAMPLE 1

Inhibitory activity against binding of GPIIb/IIIa and fibrinogen (1) Cultivation of human erythroleukemia-derived cell line (hereinafter referred to as HEL cells)

HEL cells (HEl92.1.7; ATCC No. TIB180) were purchased from ATCC (Rockville, Md., U.S.A.). The medium was RPMI medium (GIBCO Laboratories, Grand Island, N.Y., U.S.A.) containing 40 mM N-2-hydroxyethylpiperazine-N'-2-ethanesulfonic acid (hereinafter referred to as HEPES) (pH 7.0), 0.2% NaHCO$_3$, 100 µg/ml kanamycin and 10% FCS. The cells were cultured in the presence of 5% CO$_2$ at 37° C., with the medium replaced with a fresh medium to obtain a 4- to 5-fold dilution at intervals of 3 to 4 days.

(2) Purification of GPIIb/IIIa from HEL cells

GPIIb/IIIa was purified by a modification of the method of L. A. Fitzgerald et al. [J. Biol. Chem., 262, 3936 (1987)] as follows: All purification was conducted at room temperature, unless otherwise stated. At 7 days of cultivation, cells were collected from the HEL cell culture broth (cell suspension) by centrifugation (1,000×g, 10 minutes, 4° C.). After washing with 20 mM Tris-HCl (pH 7.5) containing 1 mM EDTA and 150 mM NaCl, the cells were suspended in a solubilizing buffer (20 mM Tris-HCl, 150 mM NaCl, 1% Triton X-100, 1 mM MgCl$_2$, 1 mM CaCl$_2$, 0.1 mM (p-amidinophenyl)methanesulfonyl fluoride (hereinafter referred to as APMSF), 10 nM leupeptin, 0.02% NAN$_3$, pH 7.4), followed by gentle stirring at 4° C. for 30 minutes, to solubilize the GPIIb/IIIa. The suspension was centrifuged (100,000×g, 1 hour) at 4° C., and the cell debris removed, to yield a cell extract. The cell extract was passed through a Heparin-Sepharose CL-6B column (Pharmacia LKB) and a DEAE-Toyopearl 650M column (Tosoh), both previously equilibrated with a column buffer (20 mM Tris-HCl, 150 mM NaCl, 0.1% Triton X-100, 1 mM MgCl$_2$, 1 mM CaCl$_2$, 0.1 mM APMSF, 1 nM leupeptin, 0.05% NAN$_3$, pH 7.4). The effluent was applied to a ConA-Sepharose column (Pharmacia LKB), previously equilibrated with the same column buffer as above, to adsorb the GPIIb/IIIa, followed by elution with the same column buffer but containing 0.5M methyl α-D-mannopyranoside. The eluted fraction was concentrated at 4° C. using an ultrafiltration apparatus (Amicon Corporation the fraction's molecular weight of 10,000), after which it was subjected to gel filtration through a Sephacryl S-300 column (Pharmacia LKB), previously equilibrated with the same column buffer, to yield a purified standard sample.

(3) Biotinization of human fibrinogen

Conducted by the method of I. F. Charo [I. F. Charo et al., J. Biol. Chem., 266, 1415 (1991)].

Human fibrinogen (Kabi Vitrum AB) was dissolved in PBS to 5 mg/ml and then dialyzed at 4° C. against 0.1M carbonate buffer (pH 8.2) containing 0.1M NaCl. After dialysis, insoluble substances were removed by centrifugation (100,000×g, 30 minutes), and the dialyzate was diluted to 1 mg/ml with the same buffer. To this dilution, sulfo-N-hydroxysuccinimidebiotin (Pierce Chemical Co.) was added to a final concentration of 0.2 mg/ml, followed by gentle mixing at room temperature for 30 minutes, to biotinize the fibrinogen. After completion of the reaction, the mixture was dialyzed against 0.05M Tris-HCl buffer (pH 7.4) containing 0.1M NaCl and 0.05% NAN$_3$.

(4) Determination of inhibitory activity against fibrinogen binding

Conducted by a modification of the method of I. F. Charo [I. F. Charo et al., J. Biol. Chem., 266, 1415 (1991)] as follows: The purified GPIIb/IIIa was diluted to 1 µg/ml with buffer A (20 mM Tris-HCl, 150 mM NACl, 1 mM CaCl$_2$, 0.02% NAN$_3$, pH 7.4). A 100 µl aliquot of this dilution was dispensed to a 96-well microplate (Maxisorp, produced by Nunc), and the plate kept standing at 4° C., to adsorb the GPIIb/IIIa to the microplate. Next, 150 µl of buffer B (35 mg/ml BSA, 50 mM Tris-HCl, 100 mM NaCl, 2 mM CaCl$_2$, 0.02% NAN$_3$, pH 7.4) was added, followed by 2 hours of blocking at 30° C. After microplate washing with buffer C (1 mg/ml BSA, 50 mM Tris-HCl, 100 mM NaCl, 2 mM CaCl$_2$, pH 7.4), 80 µl of buffer C, 10 µl of the sample solution and 10 µl of the 100 nM biotinized fibrinogen were added, followed by 3 hours of reaction at 30° C. or overnight reaction at room temperature.

Next, after microplate washing with 250 µl of buffer C, 100 µl of anti-biotin alkaline phosphatase conjugate (Sigma Chemical Co., diluted 1,000 folds with buffer C) was added, and the plate kept standing at 30° C. for 1 hour. After 100 µl of p-nitrophenyl phosphate solution (alkaline phosphatase coloring kit, Bio-Rad Laboratories) was added, the reaction was carried out at room temperature for 1 to 3 hours, and 100 µl of 0.4N NaOH added to stop the reaction, after which absorbance at 45 nm was determined. Fibrinogen binding inhibition (%) was calculated using the following equation:

$$\text{GPIIb/IIIa fibrinogen binding inhibition rate (\%)} = \left(1 - \frac{\text{absorbance with sample}}{\text{absorbance without sample}}\right) \times 100$$

The sample was prepared at concentrations of $1 \times 10^{-5}$M and $1 \times 10^{-6}$M, and the inhibition rate was obtained for each concentration. The results are given in Tables 1 and 2. Table 1 shows the fibrinogen binding inhibitory activities of quinolonecarboxylic acid compounds currently used as antimicrobial agents.

TABLE 1

| Compound Name | GPIIb/IIIa Fibrinogen Binding Inhibitory Activity (%) | |
|---|---|---|
| | $1 \times 10^{-5}$ M | $1 \times 10^{-6}$ M |
| Norfloxacin | 77.4 | 38.7 |
| Enoxacin | 62.0 | 24.3 |
| Cyprofloxacin | 85.5 | 47.6 |
| Romechloxaxin | 59.6 | 22.8 |
| Ofloxacin | 42.4 | 4.0 |
| Tosufloxacin | 37.6 | 30.7 |

TABLE 2

| Compound Number | $R^2$ | Z | $R^3$ | $R^4$ | $R^5$ | GPIIb/IIIa Fibrinogen Binding Inhibitory Activity (%) | |
|---|---|---|---|---|---|---|---|
| | | | | | | $10^{-5}$M | $10^{-6}$M |
| 1 | $CH_3$ | CF | −N(piperazine)N−$CH_3$ | F | H | 70.7 | 48.6 |
| 2 | $CH_3$ | CF | 4-amino-1,2,3,4-tetrahydroisoquinolin-2-yl | F | H | 72.4 | 48.4 |
| 3 | $C_2H_5$ | CH | −N(piperazine)N−(4-pyridyl) | F | H | 82.2 | 57.1 |
| 4 | $C_2H_5$ | CH | −N(piperazine)N−$CH_2$−(2-pyridyl) | F | H | 70.9 | 33.0 |
| 5 | $C_2H_5$ | CH | −S−(1-methylpiperidin-4-yl) | F | H | 60.3 | 26.0 |
| 6 | $C_2H_5$ | CF | −N(octahydropyrrolo[1,2-a]pyrazin-2-yl) | F | H | 83.3 | 39.3 |

TABLE 2-continued

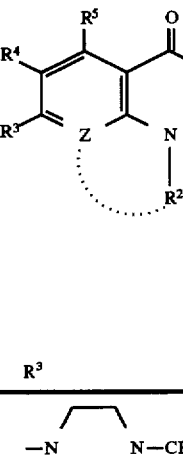

| Compound Number | R² | Z | R³ | R⁴ | R⁵ | GPIIb/IIIa Fibrinogen Binding Inhibitory Activity (%) 10⁻⁵M | 10⁻⁶M |
|---|---|---|---|---|---|---|---|
| 7 | CH₂CH₂F | CF | −N(piperazine)N−CH₃ | F | H | 91.0 | 62.1 |
| 8 | CH₂CH₂F | CF | −N(octahydropyrrolo[1,2-a]pyrazine)N | F | H | 79.3 | 53.1 |
| 9 | CH₂CH₂F | CF | −N(imidazopiperazine)N | F | H | 69.5 | 43.9 |
| 10 | CH₂CH₂OH | CF | −N(imidazopiperazine)N | F | H | 91.3 | 72.9 |
| 11 | CH₂CH₂OCONH₂ | CF | −N(piperazine)NH | F | H | 96.8 | 84.3 |
| 12 | CH₂CH₂N(CH₃)₂ | CH | −N(piperazine)NH | F | H | 79.1 | 65.1 |
| 13 | CH₂CH₂N(CH₃)₂ | CH | −N(piperazine)N−CH₃ | F | H | 70.5 | 54.7 |
| 14 | CH₂CH₂COOH | CF | −N(piperazine)NH | F | H |  | 56.1 |
| 15 | azetidine-NCOCH₃ | CF | −N(piperazine)N−CH₃ | F | H | 60.5 | 33.9 |
| 16 | azetidine-N−CH₃ | CF | −N(piperazine)N−CH₃ | F | H | 60.4 | 43.2 |

TABLE 2-continued
| Compound Number | R² | Z | R³ | R⁴ | R⁵ | GPIIb/IIIa Fibrinogen Binding Inhibitory Activity (%) | |
|---|---|---|---|---|---|---|---|
| | | | | | | 10⁻⁵M | 10⁻⁶M |
| 17 | 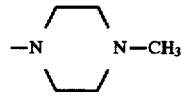 | CF |  | F | H | 47.3 | 17.1 |
| 18 | 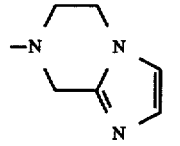 | CF |  | F | H | 42.6 | 30.5 |
| 19 | 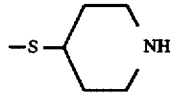 | CF |  | F | H | 49.7 | 7.0 |
| 20 | 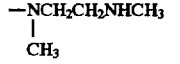 | N | —NCH₂CH₂NHCH₃<br>    \|<br>    CH₃ | F | H | 59.4 | 12.0 |
| 21 |  | N | 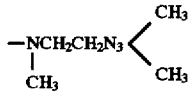 | F | H | 69.9 | 31.3 |
| 22 |  | CF | 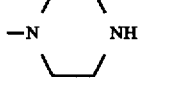 | F | H | 72.7 | 39.8 |
| 23 |  | CF | 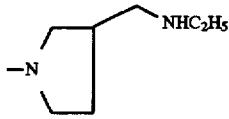 | F | H | 72.3 | 36.2 |
| 24 |  | CF | 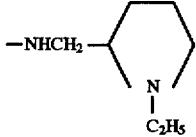 | F | H | 50.0 | 24.9 |
| 25 |  | CF | 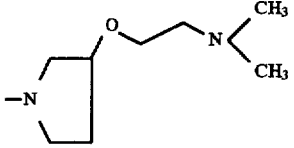 | F | H | 87.8 | 67.7 |

TABLE 2-continued
| Compound Number | R² | Z | R³ | R⁴ | R⁵ | GPIIb/IIIa Fibrinogen Binding Inhibitory Activity (%) 10⁻⁵M | 10⁻⁶M |
|---|---|---|---|---|---|---|---|
| 26 | 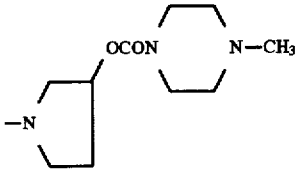 | CF |  | F | H | 94.1 | 71.4 |
| 27 | 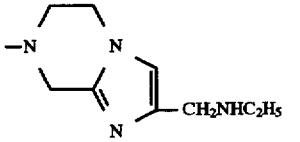 | CF |  | F | H | 78.4 | 42.6 |
| 28 | 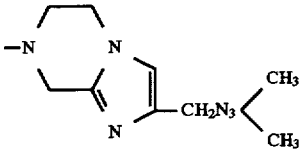 | CF |  | F | H | 95.8 | 73.3 |
| 29 | 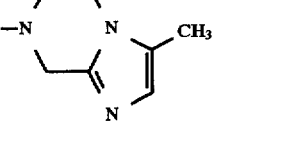 | CF |  | F | H | 68.7 | 38.4 |
| 30 | 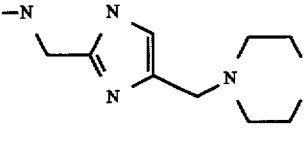 | CF |  | F | H | 54.8 | 24.2 |
| 31 | 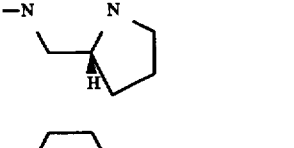 | CF |  | F | H | 73.0 | 39.3 |
| 32 | 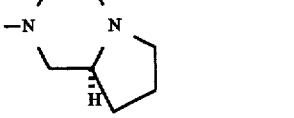 | CH |  | F | H | 71.2 | 39.5 |

TABLE 2-continued
| Compound Number | R² | Z | R³ | R⁴ | R⁵ | GPIIb/IIIa Fibrinogen Binding Inhibitory Activity (%) 10⁻⁵M | 10⁻⁶M |
|---|---|---|---|---|---|---|---|
| 33 |  | CF |  | F | H | 68.3 | 33.6 |
| 34 | 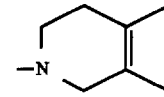 | CF |  | F | H | 77.0 | 49.4 |
| 35 | 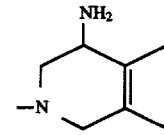 | CF |  | F | H | 51.8 | 21.5 |
| 36 | 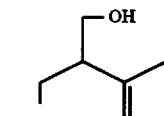 | CF |  | F | H | 56.0 | 36.3 |
| 37 | 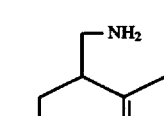 | CF |  | F | H | 60.1 | 32.5 |
| 38 | 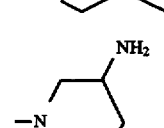 | CF |  | F | H | 50.8 | 31.9 |
| 40 | 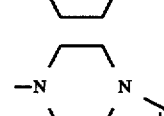 | CF |  | F | F | 50.6 | 34.7 |
| 41 | 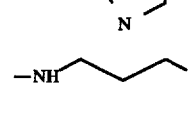 | CF | —NH(CH₂)₃C(O)—NH₂ | F | H | 58.8 | 17.9 |
| 42 |  | CF | 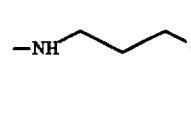 | F | H | 67.3 | 38.6 |

TABLE 2-continued
| Compound Number | R² | Z | R³ | R⁴ | R⁵ | GPIIb/IIIa Fibrinogen Binding Inhibitory Activity (%) 10⁻⁵M | 10⁻⁶M |
|---|---|---|---|---|---|---|---|
| 43 | 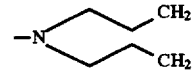 | CF |  | F | H | 52.1 | 20.2 |
| 44 | 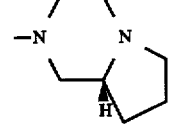 | CF | 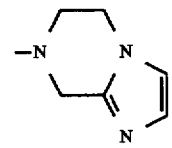 | F | NH₂ | 61.6 | 33.4 |
| 45 | OCH₃ | CF | 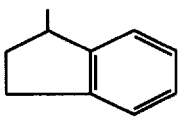 | F | H | 59.9 | 31.4 |
| 46 | 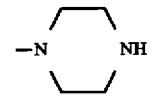 | CF | 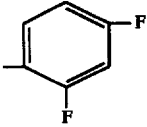 | F | H | | 41.6 |
| 47 | 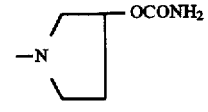 | CF |  | F | H | | 43.1 |
| 48 | 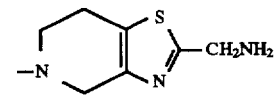 | CF | 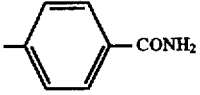 | F | H | | 57.7 |
| 49 | 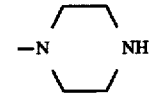 | CF | 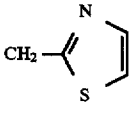 | F | H | | 30.5 |
| 50 | 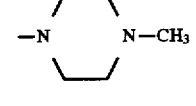 | CF | 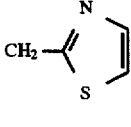 | F | H | 99.8 | 92.3 |
| 51 | 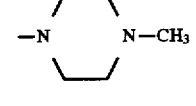 | CF | 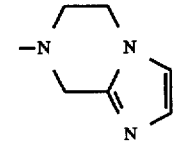 | F | H | 97.5 | 88.1 |

TABLE 2-continued
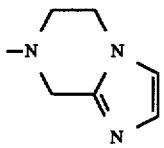
| Compound Number | R² | Z | R³ | R⁴ | R⁵ | GPIIb/IIIa Fibrinogen Binding Inhibitory Activity (%) 10⁻⁵M | 10⁻⁶M |
|---|---|---|---|---|---|---|---|
| 52 | —CH₂CH₂—O— | | 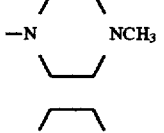 | F | H | 90.8 | 55.0 |
| 53 | —CH₂CH₂—N(CH₃)— | | 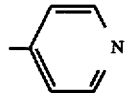 | F | H | 89.5 | 47.6 |
| 54 |  | CF | 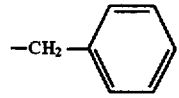 | F | H | 50.1 | 21.0 |
| 55 | —CH₂—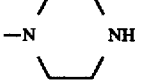 | CF | 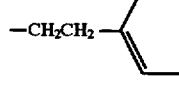 | F | H | 100 | 93.8 |
| 56 | —CH₂CH₂—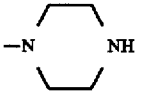 | CF | 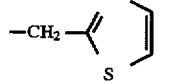 | F | H | 88.2 | 72.2 |
| 57 | —CH₂—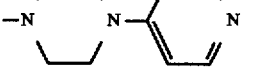 | CH | 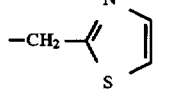 | H | H | 100 | 100 |
| 58 | —CH₂—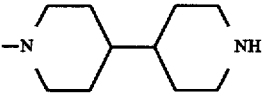 | CH | 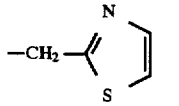 | H | H | 100 | 100 |
| 59 | —CH₂— | CF | 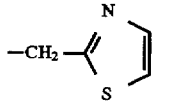 | F | H | 100 | 100 |
| 60 | —CH₂—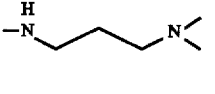 | CF | 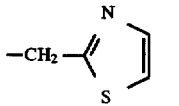 | F | H | 100 | 95.0 |
| 61 | —CH₂— | CF | —N⌒NH | F | H | 100 | 97.1 |

TABLE 2-continued

| Compound Number | R² | Z | R³ | R⁴ | R⁵ | GPIIb/IIIa Fibrinogen Binding Inhibitory Activity (%) 10⁻⁵M | 10⁻⁶M |
|---|---|---|---|---|---|---|---|
| 62 | -CH₂-(thiazol-2-yl) | CF | -N(pyrrolidinyl)-O-CH₂CH₂-N(CH₃)₂ | F | H | 100 | 100 |
| 63 | -CH₂-(thiazol-2-yl) | CF | -N(pyrrolidinyl)-O-C(O)-N(4-Me-piperazinyl) | F | H | 100 | 100 |
| 64 | -CH₂-(thiazol-2-yl) | CF | -N(piperazinyl)-(4-pyridyl) | F | H | 100 | 100 |
| 65 | -CH₂-(thiazol-2-yl) | CF | -N(piperazinyl)-(2-pyridyl) | F | H | 100 | 81.2 |
| 66 | -CH₂-(thiazol-2-yl) | CF | -N(piperazinyl)-(3-pyridyl) | F | H | 100 | 86.7 |
| 67 | -CH₂-(thiazol-2-yl) | CF | -N(piperazinyl)-(4,6-bis(pyrrolidin-1-yl)pyrimidin-2-yl) | F | H | 58.6 | 76.4 |
| 68 | -CH₂-(thiazol-2-yl) | CF | -N(4,4'-bipiperidinyl)-NH | F | H | 100 | 100 |
| 69 | -CH₂-(thiazol-2-yl) | CF | -N(piperazinyl)-CH₂CH₂-NHAc | F | H | 100 | 92.2 |
| 70 | -CH₂-(thiazol-2-yl) | CF | -N(piperazinyl)-CH₂CH₂-NH₂ | F | H | 100 | 95.9 |

TABLE 2-continued

| Compound Number | R² | Z | R³ | R⁴ | R⁵ | GPIIb/IIIa Fibrinogen Binding Inhibitory Activity (%) 10⁻⁵M | 10⁻⁶M |
|---|---|---|---|---|---|---|---|
| 71 | −CH₂−(thiazol-2-yl) | CF | −N(piperazinyl)−CH₂CH₂OH | F | H | 100 | 100 |
| 72 | −CH₂−(thiazol-4-yl) | CF | −N(piperazinyl)NH | F | H | 100 | 88.6 |
| 73 | −CH₂−(thiazol-4-yl) | CF | −N(piperazinyl)−N(pyridin-4-yl) | F | H | 100 | 100 |
| 74 | −CH₂−C₆H₄−Cl | CF | −N(piperazinyl)NH | F | H | 58.5 | 26.1 |
| 75 | −CH₂−(pyridin-4-yl) | CF | −N(piperazinyl)NH | F | H | 100 | 100 |
| 76 | −CH₂−C₆H₄−OMe (o) | CF | −N(piperazinyl)NH | F | H | 100 | 83.1 |
| 77 | −CH₂−C₆H₄−OMe (p) | CH | −N(4,4'-bipiperidinyl)NH | H | H | 94.5 | 100 |
| 78 | −CH₂−C₆H₄−F | CF | −N(4,4'-bipiperidinyl)NH | F | H | 98.1 | 100 |
| 79 | −CH₂−C₆H₄−CF₃ | CF | −N(4,4'-bipiperidinyl)NH | F | H | 100 | 100 |
| 80 | −CH₂−C₆H₄−OMe (m) | CF | −N(4,4'-bipiperidinyl)NH | F | H | 100 | 100 |

TABLE 2-continued

[Structure: quinolone core with R5, R4, R3, Z, R2, COOH substituents]

| Compound Number | R² | Z | R³ | R⁴ | R⁵ | GPIIb/IIIa Fibrinogen Binding Inhibitory Activity (%) 10⁻⁵M | 10⁻⁶M |
|---|---|---|---|---|---|---|---|
| 81 | —CH₂—C₆H₄—OMe | CH | —N(piperazinyl)NH | H | H | 100 | 100 |

Reference Example 1

1-(Thiazol-2-yl)methyl-6,7,8-trifluoro-1,4-dihydro-4-oxoquinoline-3-carboxylic acid A mixture of 6.0 g of ethyl(2,3,4,5-tetrafluorobenzoyl) acetate, 5.8 g of ethyl orthoformate and 6.3 g of acetic anhydride was refluxed for 2 hours. After distillation under reduced pressure, the residue was dissolved in 50 ml of ethanol. To this solution, 2.8 g of 2-aminomethylthiazole was added, followed by stirring for 2 hours, while ice cooling. The reaction product was added to 100 ml of ice water, and the resulting crystal was collected by filtration and dried. The 8.0 g crystal obtained was dissolved in 50 ml of dimethylformamide, and 2.0 g of 60% oily sodium hydride was added, followed by heating and stirring at 100° to 110° C. for 2 hours. The reaction product was added to 100 ml of ice water and extracted with dichloromethane (100 ml×3). The extract was washed with water and dried over anhydrous magnesium sulfate, after which the solvent was distilled off under reduced pressure, to yield 5.4 g of ethyl 1-(thiazol-2-yl)methyl-6,7,8-trifluoro-1,4-dihydro-4-oxoquinoline-3-carboxylate. Next, 5.0 g of this ester was dissolved in a mixture of 3 ml of sulfuric acid, 20 ml of acetic acid and 18 ml of water, followed by stirring at 110° to 120° C. for 1.5 hours. The reaction product was added to 100 ml of ice water to cause crystallization. The resulting crystal was collected by filtration, washed with water and dried to yield 4.4 g of the title compound.

Melting point: 213°–215° C.

NMR (CDCl₃) δ: 6.15 (1H, s), 6.18 (1H, s), 7.51 (1H, d, J=3 Hz), 7.70 (1H, d, J=3 Hz), 8.0–8.35 (1H, m), 9.25 (1H, s)

Reference Examples 2–4

The same procedure as in Reference Example 1 was followed to yield the Reference Examples 2–4 listed in Table 3.

TABLE 3

[Structure: quinolone core with R², R³, R⁴, R¹, COOH substituents]

| Reference Example Number | R¹ | R² | R³ | R⁴ | Melting point (°C.) | Molecular Formula | Elemental Analysis (%) Calcd. (Found) C | H | N |
|---|---|---|---|---|---|---|---|---|---|
| 2 | —CH₂—C₆H₅ | F | F | F | 231–233 | C₁₇H₁₀F₃NO₃ | 61.27 (61.06) | 3.02 (2.98) | 4.20 (4.22) |

TABLE 3-continued

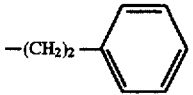

| Reference Example Number | R¹ | R² | R³ | R⁴ | Melting point (°C.) | Molecular Formula | Elemental Analysis (%) Calcd. (Found) | | |
|---|---|---|---|---|---|---|---|---|---|
| | | | | | | | C | H | N |
| 3 | —(CH₂)₂—C₆H₅ | F | F | F | 159–161 | $C_{18}H_{12}F_3NO_3$ | 62.25 (62.58) | 3.48 (3.76) | 4.03 (4.07) |
| 4 | —CH₂-(thiazol-2-yl) | H | Cl | H | 286–289 | $C_{14}H_9ClN_2O_3S$ | 52.42 (52.13) | 2.83 (2.81) | 8.73 (8.57) |

Reference Example 5

6,7,8-Trifluoro-1-(4-thiazolylmethyl)-1,4-dihydro-4-oxoquinoline-3-carboxylic acid 1.5 g of ethyl 6,7,8-trifluoro-4-hydroxyquinoline-3-carboxylate was dissolved in 30 ml of DMF, and 0.43 g of 60% oily sodium hydride was added, followed by stirring at 80° C. in a nitrogen gas stream for 20 minutes. To this solution, 1.9 g of 4-chloromethylthiazole hydrochloride was added, followed by stirring at constant temperature for 15 hours, after which the reaction mixture was concentrated to dryness. The residue was dissolved in CHCl₃; the organic layer was washed with water and dried over anhydrous magnesium sulfate and then concentrated under reduced pressure. The residue was purified by silica gel column chromatography (hexane-ethyl acetate=1:2) to yield 0.46 g of ethyl 6,7,8-trifluoro-1-(4-thiazolylmethyl)-1,4-dihydro-4-oxoquinoline-3-carboxylate as a colorless powder. This product was suspended in a mixture of acetic acid and water (3 ml:3 ml); 0.33 ml of sulfuric acid was added, followed by stirring at 120° C. for 30 minutes. The reaction mixture was allowed to cool to room temperature, and the resulting crystal was collected by filtration to yield 0.38 g of the title compound as a colorless powder.

Melting point: 240°–243° C. (decomposed)

Elemental analysis (for $C_{14}H_7F_3N_2O_3S$) Calculated (%): C, 49.42; H, 2.07; N, 8.23 Found (%): C, 48.97; H, 2.13; N, 7.97

Reference Examples 6 and 7

The same procedure as in Reference Example 5 was followed to yield the Reference Examples 6 and 7 listed in Table 4.

TABLE 4

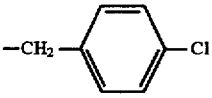

| Reference Example Number | R¹ | Melting point (°C.) | Molecular Formula | Elemental Analysis Calcd. (Found) (%) | | |
|---|---|---|---|---|---|---|
| | | | | C | H | N |
| 6 | —CH₂—C₆H₄—Cl | 260–263 | $C_{17}H_9ClF_3NO_3$ | 55.53 (55.08) | 2.47 (2.51) | 3.81 (3.63) |
| 7 | —CH₂-(pyridyl) | 228–232 (decomp.) | $C_{16}H_9F_3N_2O_3 \cdot 1/2H_2O$ | 55.99 (55.77) | 2.94 (2.74) | 8.16 (8.10) |

Reference Example 8

Ethyl 6,7,8-trifluoro-1-(2-methoxybenzyl)-1,4-dihydro-4-oxoquinoline-3-carboxylate A mixture of 2.6 g of ethyl(2,3,4,5-tetrafluorobenzoyl) acetate, 2.5 g of ethyl orthoformate and 2.7 g of acetic anhydride was refluxed for 2 hours while heating. After mixture distillation under reduced pressure, the residue was dissolved in 25 ml of ethanol and 1.4 g of 2-methoxybenzylamine was added, followed by stirring for 2 hours, while ice cooling. The reaction mixture was added to ice water, and the resulting crystal was collected by filtration. The crystal was dissolved in 25 ml of dimethylformamide and 1.0 g of 60% oily sodium hydride was added, followed by stirring at 100° C. for 2 hours. The reaction mixture was added to ice water and extracted with dichloromethane. The extract was washed with water and dried over anhydrous magnesium sulfate, after which the solvent was distilled off under reduced pressure, to yield 0.96 g of the title compound as a colorless crystal.

Melting point: 203°–204° C.

NMR (CDCl$_3$): 1.40 (3H, t, J=7 Hz), 3.80 (3H, s), 4.39 (2H, q, J=7 Hz), 5.50 (2H, d, J=3 Hz), 6.9–7.05 (3H, m), 7.3 (1H, m), 8.16 (1H, ddd, J=2.8, 10.0 Hz), 8.58 (1H, s)

Production Example 1

1-Ethyl-6-fluoro-7-[4-(4-pyridyl)piperazin-1-yl]-1,4-dihydro-4-oxoquinoline-3-carboxylic acid (compound No. 3)

A mixture of 0.31 g of 7-chloro-1-ethyl-6-fluoro-1,4-dihydro-4-oxoquinoline-3-carboxylic acid, 0.33 g of (4-pyridyl)piperazine and 2 ml of pyridine was stirred at 125° C. for 1 hour. After cooling, the reaction mixture was added to ice water to cause crystallization. The resulting crystal was collected by filtration, washed with ethyl ether and then recrystallized from ethanol to yield 0.1 g of the title compound.

Melting point: 294°–296° C. (decomposed)

Elemental analysis (for C$_{21}$H$_{21}$FN$_4$O$_3$.1/2H$_2$O) Calculated (%): C, 62.21; H, 5.47; N, 13.82 Found (%): C, 62.33; H, 5.42; N, 13.73

Production Example 2

6,8-Difluoro-7-(4-methylpiperazin-1-yl)-1-(thiazol-2-yl)methyl-1,4-dihydro-4-oxoquinoline-3-carboxylic acid hydrochloride (compound No. 50)

A mixture of 0.27 g of 1-(thiazol-2-yl)methyl-6,7,8-trifluoro-1,4-dihydro-4-oxoquinoline-3-carboxylic acid, 0.34 g of 4-methylpiperazine and 3 ml of pyridine was stirred at 100° C. for 2 hours. After the reaction mixture was concentrated under reduced pressure, 5 ml of water was added to the residue, and 1N hydrochloric acid added to obtain pH 5. The resulting crystal was collected by filtration and dried to yield 0.21 g of the title compound.

Melting point: 250°–252° C.

Elemental analysis (for C$_{19}$H$_{18}$F$_2$N$_4$O$_3$S.HCl.1/2H$_2$O) Calculated (%): C, 48.98; H, 4.33; N, 12.03 Found (%): C, 49.28; H, 4.20; N, 11.99

Production Example 3

6,7-Difluoro-7-(5,6,7,8-tetrahydroimidazo[1,2-a]pyrazin-7-yl)-1-(thiazol-2-yl)methyl-1,4-dihydro-4-oxoquinoline-3-carboxylic acid (compound No. 51)

A mixture of 0.34 g of 1-(thiazol-2-yl)methyl-6,7,8-trifluoro-1,4-dihydro-4-oxoquinoline-3-carboxylic acid, 0.5 g of 5,6,7,8-tetrahydroimidazo[1,2-a]pyrazine and 2 ml of N-methylpyrrolidone was stirred at 60° to 70° C. for 2 hours. After the reaction mixture was concentrated under reduced pressure, 10 ml of water was added to the residue, followed by extraction with chloroform (20 ml×3). After the extract was dried over anhydrous magnesium sulfate, the solvent was distilled off, and the residue was recrystallized from ethyl ether to yield 0.06 g of the title compound.

Melting point: 210°–213° C.

Elemental analysis (for C$_{20}$H$_{15}$F$_2$N$_5$O$_3$S.1/2H$_2$O) Calculated (%): C, 52.97; H, 3.56; N, 15.45 Found (%): C, 52.72; H, 3.45; N, 15.23

Production Example 4

1-(2-Carbamoyloxyethyl)-6,8-difluoro-7-(1-piperazinyl) 1,4-dihydro-4-oxoquinoline-3-carboxylic acid (compound No. 11)

A mixture of 0.24 g of 1-(2-carbamoyloxyethyl)-6,7,8-trifluoro-1,4-dihydro-4-oxoquinoline-3-carboxylic acid, 0.24 g of piperazine and 3 ml of pyridine was stirred at 100° C. for 1 hour. After the represent mixture was concentrated under reduced pressure, waster was added to the residue, and acetic acid added to obtain pH 5.0. The resulting crystal was collected by filtration, washed with water, dried and then recrystallized from hydrated methanol to yield 0.12 g of the title compound.

Melting point: 204°–206° C.

Elemental analysis (for C$_{17}$H$_{18}$F$_2$N$_4$O$_5$.2H$_2$O) Calculated (%): C, 47.22; H, 5.13; N, 12.96 Found (%): C, 47.05; H, 4.86; N, 12.86

Production Example 5

1-Cyclopropyl-6,8-difluoro-7-(2-dimethylaminomethyl-5,6,7,8-tetrahydroimidazo[1,2-a]pyrazin-7-yl)-1,4-dihydro-4-oxoquinoline-3-carboxylic acid (compound No. 28)

Using 1-cyclopropyl-6,7,8-trifluoro-1,4-dihydro-4-oxoquinoline-3-carboxylic acid and (2-dimethylaminomethyl-5,6,7,8-tetrahydroimidazo[1,2-a] pyrazine, the same procedure as in Production Example 1 was followed to yield the title compound.

Melting point: 180°–183° C.

Elemental analysis (for C$_{22}$H$_{23}$F$_2$N$_5$O$_3$.3.5H$_2$O) Calculated (%): C, 52.17; H, 5.97; N, 13.83 Found (%): C, 51.90; H, 5.63; N, 13.83

Production Example 6

1-(2-Hydroxyethyl)-6,8-difluoro-7-(5,6,7,8-tetrahydroimidazo[1,2-a]pyrazin-7-yl)-1,4-dihydro-4-oxoquinoline-3-carboxylic acid (compound No. 10)

Using 1-(2-hydroxyethyl)-6,7,8-trifluoro-1,4-dihydro-4-oxoquinoline-3-carboxylic acid and 5,6,7,8-tetrahydroimidazo[1,2-a]pyrazine, the same procedure as in Production Example 1 was followed to yield the title compound.

Melting point: 253°–255° C.

Elemental analysis (for C$_{18}$H$_{16}$F$_2$N$_4$O$_4$.1/2H$_2$O) Calculated (%): C, 54.14; H, 4.29; N, 14.03 Found (%): C, 54.29; H, 4.08; N, 13.73

Production Example 7

9-Fluoro-1-methyl-10-(4-methylpiperazin-1-yl)7-oxo-2,3-dihydro-1H,7H-pyrido[1,2,3-de]quinoxaline-6-carboxylic acid (compound No. 53)

Using 9,10-difluoro-1-methyl-7-oxo-2,3-dihydro-1H,7H-pyrido[1,2,3-de]quinoxaline-6-carboxylic acid and 4-methylpiperazine, the same procedure as in Production Example 1 was followed to yield the title compound.

Melting point: 266°–269° C.

Elemental analysis (for $C_{18}H_{21}FN_4O_3$) Calculated (%): C, 59.99; H, 5.87; N, 15.55 Found (%): C, 59.71; H, 6.01; N, 15.36

Production Example 8

6,8-Difluoro-1-(indan-1-yl)-7-(piperazin-1-yl)1,4-dihydro-4-oxoquinoline-3-carboxylic acid (compound No. 46)

Using 1-(indan-1-yl)-6,7,8-trifluoro-1,4-dihydro-4-oxoquinoline-3-carboxylic acid and piperazine, the same procedure as in Production Example 1 was followed to yield the title compound.

Melting point: 170°–173° C.

Elemental analysis (for $C_{23}H_{21}F_2N_3O_3 \cdot 1.5H_2O$) Calculated (%): C, 61.06; H, 5.35; N, 9.29 Found (%): C, 61.30; H, 5.15; N, 9.16

Production Example 9

9-Fluoro-10-(5,6,7,8-tetrahydroimidazo[1,2-a]pyrazin-7-yl)-2,3-dihydro-7-oxo-7H-pyrido[1,2,3-a][1,4]benzoxazine-6-carboxylic acid (compound No. 52)

A mixture of 0.53 g of 9,10-difluoro-2,3-dihydro-7-oxo-7H-pyrido[1,2,3-de][1,4]benzoxazine, 1.0 g of 5,6,7,8-tetrahydroimidazo[1,2-a]pyrazine and 5 ml of dimethyl sulfoxide was stirred at 100° C. for 2 hours. The reaction mixture was added to water to cause crystallization. The resulting crystal was collected by filtration and recrystallized from a chloroform-methanol (3:1) mixture to yield 94 mg of title compound.

Melting point: 265°–268° C.

Elemental analysis (for $C_{18}H_{15}FN_4O_4 \cdot 1/4H_2O$) Calculated (%): C, 57.68; H, 4.17; N, 14.95 Found (%): C, 57.58; H, 3.99; N, 14.78

Production Example 10

1-Benzyl-6,8-difluoro-7-(1-piperazinyl)-1,4-dihydro-4-oxoquinoline-3-carboxylic acid (compound No. 55)

Using 1-benzyl-6,7,8-trifluoro-1,4-dihydro-4-oxoquinoline-3-carboxylic acid, as obtained in Reference Example 2, and piperazine, the same procedure as in Production Example 1 was followed to yield the title compound.

Melting point: 222°–223° C. (decomposed)

Elemental analysis (for $C_{21}H_{19}F_2N_3O_3 \cdot 1/2H_2O$) Calculated (%): C, 61.76; H, 4.94; N, 10.29 Found (%): C, 61.69; H, 4.93; N, 10.17

Production Example 11

6,8-Difluoro-1-phenylethyl-7-(1-piperazinyl)-1,4-dihydro-4-oxoquinoline-3-carboxylic acid (compound No. 56)

Using 6,8-difluoro-1-phenylethyl-1,4-dihydro-4-oxoquinoline-3-carboxylic acid, as obtained in Reference Example 3, and piperazine, the same procedure as in Production Example 1 was followed to yield the title compound.

Melting point: 255°–257° C. (decomposed)

Elemental analysis (for $C_{22}H_{21}F_2N_3O_3 \cdot 3/4H_2O$) Calculated (%): C, 61.89; H, 5.31; N, 9.84 Found (%): C, 62.02; H, 5.83; N, 10.27

Production Example 12

7-[4-(4-Pyridyl)piperazine-1-yl]-1-(2-thiazolylmethyl)-1,4-dihydro-4-oxoquinoline-3-carboxylic acid (compound No. 57)

Using 7-chloro-1-(2-thiazolylmethyl)-1,4-dihydro-4-oxoquinoline-3-carboxylic acid, as obtained in Reference Example 4, and 1-(4-pyridyl)piperazine, the same procedure as in Production Example 1 was followed to yield the title compound.

Melting point: 273°–276° C.

Elemental analysis (for $C_{23}H_{21}N_5O_3S \cdot 1/2H_2O$) Calculated (%): C, 60.51; H, 4.86; N, 15.34 Found (%): C, 60.32; H, 5.03; N, 15.46

Production Example 13

7-[4-(4-Piperidinyl)piperidin-1-yl]-1-(2-thiazolylmethyl)-1,4-dihydro-4-oxoquinoline-3-carboxylic acid (compound No. 58)

Using 7-chloro-1-(2-thiazolylmethyl)-1,4-dihydro-4-oxoquinoline-3-carboxylic acid, as obtained in Reference Example 4, and 4,4'-bipiperidine, the same procedure as in Production Example 1 was followed to yield the title compound.

Melting point: 249°–254° C. (decomposed)

Elemental analysis (for $C_{24}H_{28}N_4O_3S \cdot H_2O$) Calculated (%): C, 61.26; H, 6.43; N, 11.91 Found (%): C, 60.89; H, 6.65; N, 11.93

Production Example 14

6,8-Difluoro-7-(1-piperazinyl)-1-(2-thiazolylmethyl)-1,4-dihydro-4-oxoquinoline-3-carboxylic acid hydrochloride (compound No. 59)

Using 6,7,8-trifluoro-1-(2-thiazolylmethyl)-1,4-dihydro-4-oxoquinoline-3-carboxylic acid, as obtained in Reference Example 1, and piperazine, the same procedure as in Production Example 1, was followed to yield the title compound.

Melting point: 269°–274° C. (decomposed)

Elemental analysis (for $C_{18}H_{16}F_2N_4O_3S \cdot HCl1/4H_2O$) Calculated (%): C, 48.33; H, 3.94; N, 12.52 Found (%): C, 48.59; H, 4.20; N, 12.69

Production Example 15

The same procedure as in Production Example 14 was followed to yield the compound Nos. 60–71 listed in Table 5.

TABLE 5

[Structure: quinolone with F at 6-position, F at 8-position, R³ at 7-position, COOH at 3-position, 4-oxo, N1-substituted with CH2-thiazole]

| Compound No. | R³ | Melting point (°C.) | Molecular Formula | Elemental Analysis Calcd. (Found) (%) C | H | N |
|---|---|---|---|---|---|---|
| 60 | -N(H)CH2CH2CH2N(CH3)2 | 165–170 | $C_{19}H_{20}F_2N_4O_3S \cdot 3/2H_2O$ | 50.77 (50.52) | 5.16 (4.95) | 12.46 (12.12) |
| 61 | -N(piperazinyl) | 284–287 | $C_{19}H_{18}F_2N_4O_3S \cdot HCl$ | 49.95 (49.83) | 4.19 (4.23) | 12.26 (12.38) |
| 62 | -N(pyrrolidinyl)-O-CH2CH2N(CH3)2 | 134–137 (decomp.) | $C_{22}H_{24}F_2N_4O_4S \cdot 7/2H_2O$ | 48.79 (49.07) | 5.77 (5.30) | 10.35 (9.86) |
| 63 | -N(pyrrolidinyl)-OC(O)-N(piperazinyl)-N-Me | 180–182 | $C_{24}H_{25}F_2N_5O_5S \cdot 1/2H_2O$ | 53.13 (52.96) | 4.83 (4.73) | 12.91 (13.02) |
| 64 | -N(piperazinyl)-(4-pyridyl) | 255–258 (decomp.) | $C_{23}H_{19}F_2N_5O_3S \cdot 1/2H_2O$ | 56.09 (56.09) | 4.09 (4.38) | 14.22 (13.90) |
| 65 | -N(piperazinyl)-(2-pyridyl) | 236–238 | $C_{23}H_{19}F_2N_5O_3S$ | 57.14 (56.82) | 3.96 (3.74) | 14.48 (14.46) |
| 66 | -N(piperazinyl)-(3-pyridyl) | 229–231 | $C_{23}H_{19}F_2N_5O_3S \cdot 1/2H_2O$ | 56.09 (56.02) | 4.09 (4.13) | 14.22 (14.24) |
| 67 | -N(piperazinyl)-(4,6-dipyrrolidinyl-pyrimidin-2-yl) | 247–249 (decomp.) | $C_{30}H_{32}F_2N_8O_3S \cdot H_2O$ | 56.24 (55.87) | 5.35 (5.19) | 17.49 (17.16) |
| 68 | -N(piperidinyl)-(4-piperidinyl)NH | 251–254 (decomp.) | $C_{24}H_{26}F_2N_4O_3S \cdot 1/2H_2O$ | 57.93 (57.75) | 5.47 (6.11) | 11.26 (11.20) |
| 69 | -N(piperazinyl)-CH2CH2NHAc | 238–240 | $C_{22}H_{23}F_2N_5O_4S$ | 53.76 (53.35) | 4.72 (4.54) | 14.25 (14.12) |

TABLE 5-continued

[Structure: quinoline scaffold with F at 6-position, R³ at 7-position, F at 8-position, 4-oxo, 3-COOH, and N1-CH₂-thiazole substituent]

| Compound No. | R³ | Melting point (°C.) | Molecular Formula | Elemental Analysis Calcd. (Found) (%) C | H | N |
|---|---|---|---|---|---|---|
| 70 | −N(piperazinyl)−CH₂CH₂−NH₂ | 192–196 (decomp.) | $C_{20}H_{21}F_2N_5O_3S$ $HCl.4H_2O$ | 43.05 (42.93) | 5.42 (5.46) | 12.55 (12.71) |
| 71 | −N(piperazinyl)−CH₂CH₂−OH | 169–171 | $C_{20}H_{20}F_2N_4O_4S$ $.1/2H_2O$ | 52.28 (51.84) | 4.61 (4.95) | 12.19 (12.05) |

Production Example 16

6,8-Difluoro-7-(1-piperazinyl)-1-(4-thiazolylmethyl)-1,4-dihydro-4-oxoquinoline-3-carboxylic acid hydrochloride (compound No. 72)

Using 6,7,8-trifluoro-1-(4-thiazolylmethyl)-1,4-dihydro-4-oxoquinoline-3-carboxylic acid, as obtained in Reference Example 5, and piperazine, the same procedure as in Production Example 1 was followed to yield the title compound.

Melting point: 271°–278° C. (decomposed)

Elemental analysis (for $C_{18}H_{16}F_2N_4O_3S.HCl.H_2O$) Calculated (%): C, 46.91; H, 4.16; N, 12.16 Found (%): C, 46.63; H, 4.00; N, 12.33

Production Example 17

6,8-Difluoro-7-[4-(4-pyridyl)piperazine-1-yl]-1-(4-thiazolylmethyl)-1,4-dihydro-4-oxoquinoline-3-carboxylic acid (compound No. 73)

Using 6,7,8-trifluoro-1-(4-thiazolylmethyl)-1,4-dihydro-4-oxoquinoline-3-carboxylic acid, as obtained in Reference Example 5, and 1-(4-pyridyl)piperazine, the same procedure as in Production Example 1 was followed to yield the title compound.

Melting point: 209°–212° C. (decomposed)

Elemental analysis (for $C_{23}H_{19}F_2N_5O_3S.7/2H_2O$) Calculated (%): C, 50.54; H, 4.79; N, 12.81 Found (%): C, 50.19; H, 4.37; N, 13.15

Production Example 18

1-(4-Chlorobenzyl)-6,8-difluoro-7-(1-piperazinyl)-1,4-dihydro-4-oxoquinoline-3-carboxylic acid (compound No. 74)

Using 1-(4-chlorobenzyl)-6,7,8-trifluoro-1,4-dihydro-4-oxoquinoline-3-carboxylic acid, as obtained in Reference Example 6, and piperazine, the same procedure as in Production Example 1 was followed to yield the title compound.

Melting point: 222°–225° C. (decomposed)

Elemental analysis (for $C_{21}H_{18}ClF_2N_3O_3.1/2H_2O$) Calculated (%): C, 56.96; H, 4.32; N, 9.49 Found (%): C, 57.14; H, 4.42; N, 9.75

Production Example 19

6,8-Difluoro-7-(1-piperazinyl)-1-(4-pyridylmethyl)-1,4-dihydro-4-oxoquinoline-3-carboxylic acid (compound No. 75)

Using 6,7,8-trifluoro-1-(4-pyridylmethyl)-1,4-dihydro-4-oxoquinoline-3-carboxylic acid, as obtained in Reference Example 7, and piperazine, the same procedure as in Production Example 1 was followed to yield the title compound.

Melting point: 256°–259° C. (decomposed)

Elemental analysis (for $C_{20}H_{18}F_2N_4O_3.3H_2O$) Calculated (%): C, 52.86; H, 5.32; N, 12.33 Found (%): C, 52.98; H, 5.05; N, 11.97

Production Example 20

6,8-Difluoro-1-(2-methoxybenzyl)-7-(1-piperazinyl)-1,4-dihydro-4-oxoquinoline-3-carboxylic acid (compound No. 76)

0.5 g of ethyl 6,7,8-trifluoro-1-(2-methoxybenzyl)-1,4-dihydro-4-oxoquinoline-3-carboxylate, as obtained in Reference Example 8, was suspended in 5 ml of pyridine; 0.32 g of piperazine (anhydrous) was added, followed by stirring at 90° C. for 2 hours. After the reaction mixture was allowed to cool, water was added, and the resulting crystal was collected by filtration. The crystal was dissolved in 5 ml of methanol and 1.3 ml of 1N aqueous sodium hydroxide was added, followed by stirring at 55° C. for 30 minutes. After the methanol was distilled off under reduced pressure, water was added to the residue, and acetic acid was added to obtain pH 6. The resulting crystal was collected by filtration to yield 264 mg of the title compound as a colorless crystal.

Melting point: 209°–211° C. (decomposed)

Elemental analysis (for $C_{22}H_{21}F_2N_3O_4.1/2H_2O$) Calculated (%): C, 60.27; H, 5.06; N, 9.58 Found (%): C, 60.83; H, 5.43; N, 9.33

Production Example 21

1-(4-Methoxybenzyl)-7-[4-(4-piperidinyl)piperidin-1-yl]-1,4-dihydro-4-oxoquinoline-3-carboxylic acid (compound No. 77)

Using 7-chloro-4-hydroxyquinoline-3-carboxylic acid, 4-methoxybenzyl chloride and 4,4'-bipiperidine dihydrochloride, the same procedure as in Reference Example 5 and Production Example 1 was followed to yield the title compound as a colorless crystal.

Melting Point: 207°–211° C.

Elemental analysis (for $C_{28}H_{33}N_3O_4.2H_2O$) Calculated (%): C, 65.73; H, 7.29; N, 8.21 Found (%): C, 65.48; H, 7.23; N, 7.96

Production Example 22

6,8-Difluoro-1-(4-fluorobenzyl)-7-[4-(4-piperidinyl) piperidin-1-yl]-1,4-dihydro-4-oxoquinoline-3-carboxylic acid (compound No. 78)

Using 4-fluorobenzyl chloride and 4,4'-bipiperidine dihydrochloride, the same procedure as in Reference Example 5 and Production Example 1 was followed to yield the title compound as a colorless crystal.

Melting Point: 224°–248° C.

Elemental analysis (for $C_{27}H_{28}F_3N_3O_3.2H_2O$) Calculated (%): C, 60.55; H, 6.02; N, 7.85 Found (%): C, 60.85; H, 5.80; N, 7.52

Production Example 23

6,8-Difluoro-7-[4-(4-piperidinyl)piperidin-1-yl]-1-(4-trifluoromethylbenzyl)-1,4-dihydro-4-oxoquinoline-3-carboxylic acid (compound No. 79)

Using 4-trifluoromethylbenzyl bromide and 4,4'-bipiperidine dihydrochloride, the same procedure as in Reference Example 5 and Production Example 1 was followed to yield the title compound as a colorless crystal.

Melting Point: 224°–226° C.

Elemental analysis (for $C_{28}H_{28}F_5N_3O_3.H_2O$) Calculated (%): C, 59.26; H, 5.33; N, 7.40 Found (%): C, 58.98; H, 5.26; N, 7.41

Production Example 24

6,8-Difluoro-1-(3-methoxybenzyl)-7-[4-(4-piperidinyl) piperidin-1-yl]-1,4-dihydro-4-oxoquinoline-3-carboxylic acid (compound No. 80)

Using 3-methoxybenzyl chloride and 4,4'-bipiperidine dihydrochloride, the same procedure as in Reference Example 5 and Production Example 1 was followed to yield the title compound as a colorless crystal.

Melting Point: 256°–260° C. (decomposed)

Elemental analysis (for $C_{28}H_{31}F_2N_3O_4.H_2O$) Calculated (%): C, 63.50; H, 6.28; N, 7.93 Found (%): C, 63.49; H, 6.08; N, 8.15

Production Example 25

1-(4-Methoxybenzyl)-7-(piperazin-1-yl)-1,4-dihydro-4-oxoquinoline-3-carboxylic acid (compound No. 81)

Using 4-methoxybenzyl chloride and piperazine, the same procedure as in Reference Example 5 and Production Example 1 was followed to yield the title compound as a colorless crystal.

Melting Point: 230°–235° C.

Elemental analysis (for $C_{22}H_{23}N_3O_4.2H_2O$) Calculated (%): C, 61.53; H, 6.34; N, 9.78 Found (%): C, 61.35; H, 6.09; N, 10.04

EXAMPLE 1

| | |
|---|---|
| (1) Compound No. 50 | 50 g |
| (2) Lactose | 100 g |
| (3) Corn starch | 15 g |
| (4) Carboxymethyl cellulose calcium | 44 g |
| (5) Magnesium stearate | 1 g |
| 1,000 tablets | 210 g |

The entire amounts of components (1), (2) and (3) and 30 g of component (4) were kneaded with water and vacuum dried, followed by granulation. This granulated powder was mixed with 14 g of component (4) and 1 g of component (1) and tableted using a tableting machine to yield 1,000 tablets containing 50 mg of component (1) per tablet.

EXAMPLE 2

The following components were mixed and dissolved to yield an ampule of injection.

| | Per Ampule |
|---|---|
| Compound No. 50 | 50 mg |
| Sodium chloride | 18 mg |
| Distilled water for injection | Appropriate amount |
| Total | 2 ml |

What is claimed is:

1. A compound of the formula:

(V)

wherein $R^1$ is hydrogen or a carboxy protecting group; $R^3$ is 4-(4-pyridyl)piperazin-1-yl group; 4-(4-piperidinyl)piperidin-1-yl group; or a group represented by the formula:

wherein $n^3$ is an integer of 1 to 4; $n^4$ is 0 or 1; and $n^5$ is a whole number 0 to 3; $R^{14}$ and $R^{15}$ are hydrogen or halogen; $R^{17}$ is an optionally substituted phenyl group; or a salt thereof.

2. A compound claimed in claim 1, wherein $R^3$ is 4-(4-pyridyl)piperazin-1-yl group or 4-(4-piperidinyl)piperidin-1-yl group and $R^{17}$ is a phenyl group which may be substituted with 1 to 3 substituents selected from hydroxy, lower alkoxy, halogen and trifluoromethyl.

3. 1-Benzyl-6,8-difluoro-7-(1-piperazinyl)-1,4-dihydro-4-oxoquinoline-3-carboxylic acid.

4. 1-(4-Chlorobenzyl)-6,8-difluoro-7-(1-piperazinyl)-1,4-dihydro-4-oxoquinoline-3-carboxylic acid.

5. 6,8-Difluoro-1-(2-methoxybenzyl)-7-(1-piperazinyl)-1,4-dihydro-4-oxoquinoline-3-carboxylic acid.

6. 1-(4-methoxybenzyl)-7-(piperazin-1-yl)-1,4-dihydro-4-oxoquinoline-3-carboxylic acid or a salt thereof.

7. A cell adhesion inhibitory composition which comprises a compound an claimed in claim 1 and a pharmaceutically acceptable carrier, diluent or excipient.

8. A method for producing a compound as claimed in claim 1, which comprises reacting a compound of the formula:

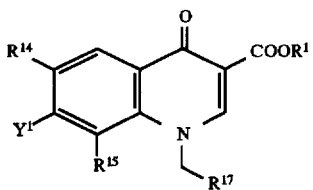
wherein $R^1$ is hydrogen or a carboxyl protecting group; $R^{14}$ and $R^{15}$ are hydrogen or halogen; $R^{17}$ is an optionally substituted phenyl group; and $Y^1$ is halogen; or a salt thereof, with a compound of the formula:
$$R^3\text{—H}$$
wherein $R^3$ is an organic group as defined in claim 1; or a salt thereof, to produce the compound as claimed in claim 1, or a salt thereof.
* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE:

```
( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:1:

Gly Arg Gly Asp Ser Pro
 1               5
```